United States Patent
Maekawa et al.

(10) Patent No.: US 7,223,791 B2
(45) Date of Patent: May 29, 2007

(54) FUNCTION REGULATOR FOR RETINOID RELATIVE RECEPTOR

(75) Inventors: Tsuyoshi Maekawa, Nara (JP); Jun Kunitomo, Ikeda (JP); Hiroyuki Odaka, Kobe (JP); Hiroyuki Kimura, Sakai (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 491 days.

(21) Appl. No.: 10/481,033

(22) PCT Filed: Jun. 25, 2002

(86) PCT No.: PCT/JP02/06349

§ 371 (c)(1),
(2), (4) Date: Dec. 16, 2003

(87) PCT Pub. No.: WO03/000249

PCT Pub. Date: Jan. 3, 2003

(65) Prior Publication Data

US 2004/0157881 A1    Aug. 12, 2004

(30) Foreign Application Priority Data

Jun. 26, 2001    (JP) .............................. 2001-192601

(51) Int. Cl.
*A61K 31/341*    (2006.01)
(52) U.S. Cl. ..................................... 514/461
(58) Field of Classification Search ................. 514/461
See application file for complete search history.

(56) References Cited

U.S. PATENT DOCUMENTS 5,977,108 A * 11/1999 Kikuchi et al. ............. 514/249
6,020,339 A *  2/2000 Perrier et al. ............... 514/269

FOREIGN PATENT DOCUMENTS

WO    WO 97/02244    1/1997
WO    WO 97/34869    9/1997
WO    WO 00/01679    1/2000

OTHER PUBLICATIONS

Bruno et al., Expert Opinion Emerging Drugs, (2005), 10(4), pp. 747-771.*
Park, Diabetes Research and Clinical Practice 66S (2004), S33-S35.*
Brooks, et al. "Design and Synthesis of 2-Methyl-2-{4-[2-(5-methyl-2-aryloxazol-4-yl)ethoxy]phenoxy}propionic Acids: A New Class of Dual PPARα/γ Agonists" Journal of Medicinal Chemistry 44(13): 2061-2064(2001).
Willson, et al. "The PPARs: From Orphan Receptors to Drug Discovery" Journal of Medicinal Chemistry 43(4): 527-550(2000).

* cited by examiner

*Primary Examiner*—Laura L. Stockton
(74) *Attorney, Agent, or Firm*—Edwards Angell Palmer & Dodge LLP; David G. Conlin; Lisa Swiszcz Hazzard

(57) ABSTRACT

The present invention provides a retinoid-related receptor (except retinoic acid receptors) function regulating agent comprising a compound represented by the formula:

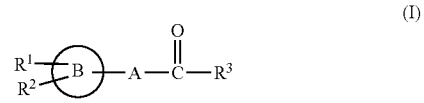

wherein one of $R^1$ and $R^2$ is an optionally substituted monocyclic aromatic hydrocarbon group or an optionally substituted monocyclic aromatic heterocyclic group containing one heteroatom, and the other is a hydrogen atom and the like; B is a 5- or 6-membered heterocycle (except 1,3-azole); A is an optionally substituted aromatic hydrocarbon group or an optionally substituted aromatic heterocyclic group; and $R^3$ is a hydrogen atom and the like, or a salt thereof, which is useful as an agent for the prophylaxis or treatment of diabetes mellitus, hyperlipidemia, impaired glucose tolerance or the like.

1 Claim, No Drawings

FUNCTION REGULATOR FOR RETINOID RELATIVE RECEPTOR

This application is the National Phase filing of International Patent Application No. PCT/JP02/06349, filed Jun. 25, 2002.

TECHNICAL FIELD

The present invention relates to a retinoid-related receptor function regulating agent useful as an agent for the prophylaxis or treatment of diabetes mellitus, hyperlipidemia, impaired glucose tolerance or the like.

BACKGROUND ART

As the retinoid-related receptor function regulating agents, compounds described in the following references are known.

(1) WO 00/01679 describes, as a retinoid-related receptor function regulating agent, a 1,3-azole derivative represented by the formula:

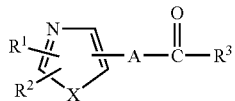

wherein $R^1$ is an optionally substituted aromatic hydrocarbon group or an optionally substituted aromatic heterocyclic group; $R^2$ is a hydrogen atom or an optionally substituted hydrocarbon group; X is O, S or a group of the formula: —$NR^4$— ($R^4$ is a hydrogen atom or an optionally substituted alkyl group); A is an optionally substituted aromatic hydrocarbon group or an optionally substituted aromatic heterocyclic group; and $R^3$ is a group of the formula: —$OR^5$ ($R^5$ is a hydrogen atom or an optionally substituted hydrocarbon group) or —$NR^6R^7$ ($R^6$ and $R^7$ are the same or different and each is a hydrogen atom or an optionally substituted hydrocarbon group, $R^6$ and $R^7$ may form a ring together with the adjacent nitrogen atom).

(2) WO 97/34869 describes, as a pharmaceutical agent having retinoic acid receptor agonism, a fused ring-containing carboxylic acid derivative represented by the formula:

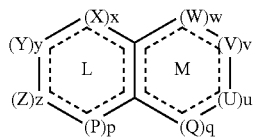

wherein ----- is a single bond or a double bond, in the formula, X, Y, Z, P, Q, U, V and W are each a group of the formula: —O—, a group of the formula: —S— or a group of the formula:

wherein $R^k$ (k: 1–8) is a hydrogen atom, a halogen atom, a lower alkyl group optionally having substituents and the like, and one of $R^7$ and $R^8$ is a group of the formula:

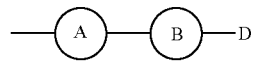

(ring A and ring B are each independently an aromatic hydrocarbon ring or unsaturated heterocycle, each of which optionally has substituents, and D is a carboxyl group optionally having a protecting group).

(3) WO 97/02244 describes, as a new retinoid-related compound replacing retinoic acid, a heterocycle containing carboxylic acid derivative represented by the formula: A-B-$(D)_{n1}$-(C=O)-M wherein A is a heteroaryl group which has at least one nitrogen atom and optionally has substituents, and the like, B is a heteroarylene group, a group of —CONH—, a group of —$CR^6$=$CR^7$— ($R^6$ and $R^7$ are each H, a lower alkyl group etc.), and the like, D is an arylene group, a heteroarylene group and the like, n1 is 0 or 1, M is a hydroxyl group, a lower alkoxy group and the like.

Peroxisome proliferator-activated receptor gamma (PPARγ), a member of the intranuclear hormone receptor superfamily, which is typically exemplified by steroid hormone receptors and thyroid hormone receptors, plays an important role as a master regulator in the differentiation of adipocytes with its expression induced in the very early stage of adipocyte differentiation. PPARγ forms a dimer with retinoid X receptor (RXR) by binding to a ligand, and binds to a responsive site of the target gene in the nucleus to directly control (activate) transcription efficiency. In recent years, the possibility that 15-deoxy-$\Delta^{12.14}$ prostaglandin $J_2$, which is a metabolite of prostaglandin $D_2$, serves as an endogenous ligand for PPARγ, has been suggested, and it has been shown that a class of insulin sensitizers, typically exemplified by thiazolidinedione derivatives, possess ligand activity for PPARγ, and that its potency is proportional to its glucose-lowering action or adipocyte differentiation-promoting action [*Cell*, vol. 83, p. 803 (1995); *The Journal of Biological Chemistry*, vol. 270, p. 12953 (1995); *Journal of Medicinal Chemistry*, vol. 39, p. 655 (1996)]. Furthermore, in recent years, it has been shown that 1) PPARγ is expressed in cultured cells of human liposarcoma origin, whose proliferation is ceased by the addition of a PPARγ ligand [*Proceedings of the National Academy of Sciences of the United States of America*, vol. 94, p. 237 (1997)], 2) nonsteroidal anti-inflammatory drugs, typically exemplified by indomethacin and fenoprofen, have PPARγ ligand activity [*The Journal of Biological Chemistry*, vol. 272, p. 3406 (1997)], 3) PPARγ is expressed at high levels in activated macrophages, with the transcription of a gene involved in inflammation inhibited by the addition of a ligand therefor [*Nature*, vol. 391, p. 79 (1998)], and 4) PPARγ ligands suppress the production of inflammatory cytokines (TNFα, IL-1β, IL-6) by monocytes [*Nature*, vol. 391, p. 82 (1998)] and the like.

DISCLOSURE OF THE INVENTION

There is a demand for the development of a retinoid-related receptor function regulating agent useful as an agent for the prophylaxis or treatment of diabetes mellitus, hyperlipidemia, impaired glucose tolerance or the like, which has superior properties as a pharmaceutical agent, such as a fewer side effects and the like.

The present inventors have found that a compound having, on a 5- or 6-membered heterocycle (except 1,3-azole), specific substituents of $R^1$, $R^2$ and -A(C=O)$R^3$ [one of $R^1$ and $R^2$ is an optionally substituted monocyclic aromatic hydrocarbon group or an optionally substituted monocyclic aromatic heterocyclic group containing one heteroatom, and the other is a hydrogen atom, a halogen atom or an optionally substituted hydrocarbon group; A is an optionally substituted aromatic hydrocarbon group or an optionally substituted aromatic heterocyclic group; $R^3$ is a hydrogen atom, —$OR^4$ ($R^4$ is a hydrogen atom or an optionally substituted hydrocarbon group) or —$NR^5R^6$ ($R^5$ and $R^6$ are the same or different and each is a hydrogen atom or an, optionally substituted hydrocarbon group, or $R^5$ and $R^6$ may form an optionally substituted ring together with the adjacent nitrogen atom)] unexpectedly has a superior peroxisome proliferator-activated receptor transcriptional activity-promoting action, based on which finding, studied further and completed the present invention.

Accordingly, the present invention relates to 1) a retinoid-related receptor (except retinoic acid receptors) function regulating agent, which comprises a compound represented by the formula:

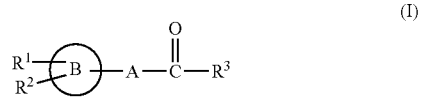

(I)

wherein
one of $R^1$ and $R^2$ is an optionally substituted monocyclic aromatic hydrocarbon group or an optionally substituted monocyclic aromatic heterocyclic group containing one heteroatom, and the other is a hydrogen atom, a halogen atom or an optionally substituted hydrocarbon group;
B is a 5- or 6-membered heterocycle (except 1,3-azole);
A is an optionally substituted aromatic hydrocarbon group or an optionally substituted aromatic heterocyclic group; and
$R^3$ is a hydrogen atom, —$OR^4$ ($R^4$ is a hydrogen atom or an optionally substituted hydrocarbon group) or —$NR^5R^6$ ($R^5$ and $R^6$ are the same or different and each is a hydrogen atom or an optionally substituted hydrocarbon group, or $R^5$ and $R^6$ may form an optionally substituted ring together with the adjacent nitrogen atom),
or a salt thereof;
2) the agent of the aforementioned 1), wherein the retinoid-related receptor is a peroxisome proliferator-activated receptor;
3) an agent for the prophylaxis or treatment of diabetes mellitus, which comprises a peroxisome proliferator-activated receptor transcriptional activity promoter which is non-binding to peroxisome proliferator-activated receptors;
4) an agent for the prophylaxis or treatment of hyperlipidemia, which comprises a peroxisome proliferator-activated receptor transcriptional activity promoter which is non-binding to peroxisome proliferator-activated receptors;
5) an agent for ameliorating lipid metabolism, which comprises a peroxisome proliferator-activated receptor transcriptional activity promoter which is non-binding to peroxisome proliferator-activated receptors;
6) an agent for the prophylaxis or treatment of obesity, which comprises a peroxisome proliferator-activated receptor transcriptional activity promoter which is non-binding to peroxisome proliferator-activated receptors;
7) an insulin sensitizer comprising a peroxisome proliferator-activated receptor transcriptional activity promoter which is non-binding to peroxisome proliferator-activated receptors;
8) an agent for improving insulin resistance, which comprises a peroxisome proliferator-activated receptor transcriptional activity promoter which is non-binding to peroxisome proliferator-activated receptors;
9) an agent for the prophylaxis or treatment of impaired glucose tolerance, which comprises a peroxisome proliferator-activated receptor transcriptional activity promoter which is non-binding to peroxisome proliferator-activated receptors;
10) a method for regulating a retinoid-related receptor (except retinoic acid receptors) function in a mammal, which comprises administering a compound represented by the formula (I) or a salt thereof to the mammal;
11) a method for the prophylaxis or treatment of diabetes mellitus in a mammal, which comprises administering, to the mammal, a peroxisome proliferator-activated receptor transcriptional activity promoter which is non-binding to peroxisome proliferator-activated receptors;
12) a method for the prophylaxis or treatment of hyperlipidemia in a mammal, which comprises administering, to the mammal, a peroxisome proliferator-activated receptor transcriptional activity promoter which is non-binding to peroxisome proliferator-activated receptors;
13) a method for ameliorating lipid metabolism in a mammal, which comprises administering, to the mammal, a peroxisome proliferator-activated receptor transcriptional activity promoter which is non-binding to peroxisome proliferator-activated receptors;
14) a method for the prophylaxis or treatment of obesity in a mammal, which comprises administering, to the mammal, a peroxisome proliferator-activated receptor transcriptional activity promoter which is non-binding to peroxisome proliferator-activated receptors;
15) a method for sensitizing insulin in a mammal, which comprises administering, to the mammal, a peroxisome proliferator-activated receptor transcriptional activity promoter which is non-binding to peroxisome proliferator-activated receptors;
16) a method for improving insulin resistance in a mammal, which comprises administering, to the mammal, a peroxisome proliferator-activated receptor transcriptional activity promoter which is non-binding to peroxisome proliferator-activated receptors;
17) a method for the prophylaxis or treatment of impaired glucose tolerance in a mammal, which comprises administering, to the mammal, a peroxisome proliferator-activated receptor transcriptional activity promoter which is non-binding to peroxisome proliferator-activated receptors;
18) use of a compound represented by the formula (I) or a salt thereof for the production of a retinoid-related receptor (except retinoic acid receptors) function regulating agent;
19) use of a peroxisome proliferator-activated receptor transcriptional activity promoter which is non-binding to peroxisome proliferator-activated receptors, for the production of an agent for the prophylaxis or treatment of diabetes mellitus;
20) use of a peroxisome proliferator-activated receptor transcriptional activity promoter which is non-binding to peroxisome proliferator-activated receptors, for the production of an agent for the prophylaxis or treatment of hyperlipidemia;
21) use of a peroxisome proliferator-activated receptor transcriptional activity promoter which is non-binding to peroxisome proliferator-activated receptors, for the production of an agent for ameliorating lipid metabolism;
22) use of a peroxisome proliferator-activated receptor transcriptional activity promoter which is non-binding to peroxisome proliferator-activated receptors, for the production of an agent for the prophylaxis or treatment of obesity;

23) use of a peroxisome proliferator-activated receptor transcriptional activity promoter which is non-binding to peroxisome proliferator-activated receptors, for the production of an insulin sensitizer;

24) use of a peroxisome proliferator-activated receptor transcriptional activity promoter which is non-binding to peroxisome proliferator-activated receptors, for the production of an agent for improving insulin resistance;

25) use of a peroxisome proliferator-activated receptor transcriptional activity promoter which is non-binding to peroxisome proliferator-activated receptors, for the production of an agent for the prophylaxis or treatment of impaired glucose tolerance; and the like.

As preferable examples of the compound represented by the formula (I), the following compounds can be mentioned.

Furan derivatives represented by the formula:

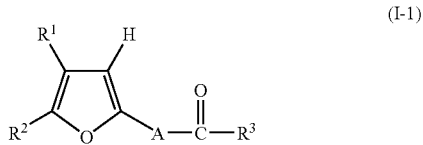

(I-1)

wherein one of $R^1$ and $R^2$ is an optionally substituted monocyclic aromatic hydrocarbon group or an optionally substituted monocyclic aromatic heterocyclic group containing one heteroatom, and the other is a hydrogen atom, a halogen atom or an optionally substituted hydrocarbon group;

A is an optionally substituted aromatic hydrocarbon group or an optionally substituted aromatic heterocyclic group; and $R^3$ is a hydrogen atom, $-OR^4$ ($R^4$ is a hydrogen atom or an optionally substituted hydrocarbon group) or $-NR^5R^6$ ($R^5$ and $R^6$ are the same or different and each is a hydrogen atom or an optionally substituted hydrocarbon group, or $R^5$ and $R^6$ may form an optionally substituted ring together with the adjacent nitrogen atom, provided that the optionally substituted monocyclic aromatic hydrocarbon group and the optionally substituted hydrocarbon group for $R^1$ or $R^2$ are not a 3,4-dimethoxyphenyl group, a 4-pentyloxyphenyl group and a phenyl group substituted by an optionally alkyl-esterified carboxyl group, or a salt thereof.

Thiophene derivatives represented by the formula:

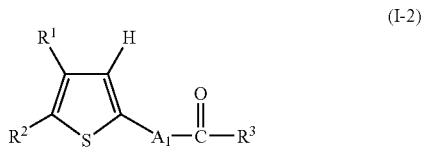

(I-2)

wherein one of $R^1$ and $R^2$ is an optionally substituted monocyclic aromatic hydrocarbon group or an optionally substituted monocyclic aromatic heterocyclic group containing one heteroatom, and the other is a hydrogen atom, a halogen atom or an optionally substituted hydrocarbon group;

$A_1$ is an optionally substituted aromatic hydrocarbon group or an optionally substituted aromatic heterocyclic group by a substituent except an optionally esterified carboxyl group; and $R^3$ is a hydrogen atom, $-OR^4$ ($R^4$ is a hydrogen atom or an optionally substituted hydrocarbon group) or $-NR^5R^6$ ($R^5$ and $R^6$ are the same or different and each is a hydrogen atom or an optionally substituted hydrocarbon group, or $R^5$ and $R^6$ may form an optionally substituted ring together with the adjacent nitrogen atom), provided that the optionally substituted monocyclic aromatic hydrocarbon group and the optionally substituted hydrocarbon group for $R^1$ or $R^2$ are not a phenyl group optionally having a substituent at the 4-position and a phenyl group substituted by an optionally alkyl-esterified carboxyl group; and the optionally substituted monocyclic aromatic heterocyclic group containing one heteroatom for $R^1$ or $R^2$ is not a substituted thienyl group), or a salt thereof.

Pyrrole derivatives represented by the formula:

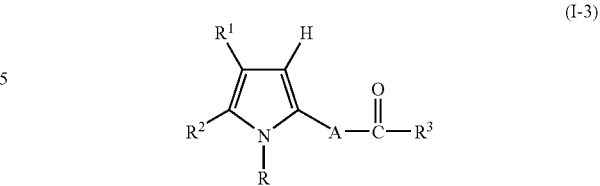

(I-3)

wherein one of $R^1$ and $R^2$ is an optionally substituted monocyclic aromatic hydrocarbon group or an optionally substituted monocyclic aromatic heterocyclic group containing one heteroatom, and the other is a hydrogen atom, a halogen atom or an optionally substituted hydrocarbon group;

A is an optionally substituted aromatic hydrocarbon group or an optionally substituted aromatic heterocyclic group;

$R^3$ is a hydrogen atom, $-OR^4$ ($R^4$ is a hydrogen atom or an optionally substituted hydrocarbon group) or $-NR^5R^6$ ($R^5$ and $R^6$ are the same or different and each is a hydrogen atom or an optionally substituted hydrocarbon group, or $R^5$ and $R^6$ may form an optionally substituted ring together with the adjacent nitrogen atom), and R is an optionally substituted hydrocarbon group, provided that when one of $R^1$ and $R^2$ is an optionally substituted phenyl group, then the other should not be pyridyl, or a salt thereof.

The definition of each substituent in the formulas (I), (I-1), (I-2), (I-3) and the like is described in detail in the following.

As the "monocyclic aromatic hydrocarbon group" of the "optionally substituted monocyclic aromatic hydrocarbon group" for $R^1$ and $R^2$, for example, a phenyl group can be mentioned.

As the "monocyclic aromatic heterocyclic group containing one heteroatom" of the "optionally substituted monocyclic aromatic heterocyclic group containing one heteroatom" for $R^1$ and $R^2$, for example, a 5- to 7-membered monocyclic aromatic heterocyclic group containing, as ring-constituting atoms, besides carbon atoms, one heteroatom selected from an oxygen atom, a sulfur atom and a nitrogen atom can be mentioned.

Specific examples of the monocyclic aromatic heterocyclic group include furyl (2-furyl, 3-furyl), thienyl (2-thienyl, 3-thienyl), pyrrolyl (1-pyrrolyl, 2-pyrrolyl, 3-pyrrolyl), pyridyl (2-pyridyl, 3-pyridyl, 4-pyridyl) and the like.

The "monocyclic aromatic hydrocarbon group" and the "monocyclic aromatic heterocyclic group containing one heteroatom" for $R^1$ and $R^2$ each optionally have 1 to 5, preferably 1 to 3, substituents at substitutable positions. As such substituent, for example, a "halogen atom", a "nitro group", an "optionally substituted hydrocarbon group", an "optionally substituted aromatic heterocyclic group", an "optionally substituted non-aromatic heterocyclic group", an "acyl group", an "optionally substituted amino group", an "optionally substituted hydroxy group", an "optionally substituted thiol group", an "optionally esterified or amidated carboxyl group" and the like can be mentioned.

As the "halogen atom", fluorine, chlorine, bromine and iodine can be mentioned, with preference given to fluorine and chlorine.

As the hydrocarbon group of the "optionally substituted hydrocarbon groups", an aliphatic hydrocarbon group, an alicyclic hydrocarbon group, an alicyclic-aliphatic hydrocarbon group, an aromatic-aliphatic hydrocarbon group and an aromatic hydrocarbon group can be mentioned. These hydrocarbon groups preferably have 1 to 14 carbon atoms.

As the aliphatic hydrocarbon group, an aliphatic hydrocarbon group having 1 to 10 carbon atoms is preferable. As the aliphatic hydrocarbon group, a saturated aliphatic hydrocarbon group having 1 to 10 carbon atoms (e.g., an alkyl group etc.), such as methyl, ethyl, propyl, isopropyl, butyl, isobutyl, sec.-butyl, t.-butyl, pentyl, isopentyl, neopentyl, hexyl, isohexyl, heptyl, octyl, nonyl and the like; an unsaturated aliphatic hydrocarbon group having 2 to 10 carbon atoms (e.g., an alkenyl group having 2 to 10 carbon atoms, an alkadienyl group having 4 to 10 carbon atoms, an alkynyl group having 2 to 10 carbon atoms, an alkadiynyl group having 4 to 10 carbon atoms etc.), such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl and the like can be mentioned.

As the alicyclic hydrocarbon group, an alicyclic hydrocarbon group having 3 to 7 carbon atoms is preferable. As the alicyclic hydrocarbon group, a saturated alicyclic hydrocarbon group having 3 to 7 carbon atoms (e.g., a cycloalkyl group etc.), such as cyclopropyl, cyclobutyl, cyclopentyl, cyclohexyl, cycloheptyl and the like; and an unsaturated alicyclic hydrocarbon group having 5 to 7 carbon atoms (e.g., a cycloalkenyl group, a cycloalkadienyl group etc.), such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl and the like can be mentioned.

As the alicyclic-aliphatic hydrocarbon group, an alicyclic-aliphatic hydrocarbon group wherein the above-mentioned alicyclic hydrocarbon group and aliphatic hydrocarbon group are linked to each other (e.g., a cycloalkyl-alkyl group, a cycloalkenyl-alkyl group etc.) can be mentioned. Of these, an alicyclic-aliphatic hydrocarbon group having 4 to 9 carbon atoms is preferable. As the alicyclic-aliphatic hydrocarbon group, for example, cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl and the like can be mentioned.

As the aromatic-aliphatic hydrocarbon group, an aromatic-aliphatic hydrocarbon group having 7 to 13 carbon atoms (e.g., an aralkyl group having 7 to 13 carbon atoms, an arylalkenyl group having 8 to 13 carbon atoms, etc.) is preferable. As the aromatic-aliphatic hydrocarbon group, for example, phenylalkyl having 7 to 9 carbon atoms such as benzyl, phenethyl, 1-phenylethyl, 1-phenylpropyl, 2-phenylpropyl, 3-phenylpropyl and the like; naphthylalkyl having 11 to 13 carbon atoms such as α-naphthylmethyl, α-naphthylethyl, β-naphthylmethyl, β-naphthylethyl and the like; phenylalkenyl having 8 to 10 carbon atoms such as styryl and the like; naphthylalkenyl having 12 to 13 carbon atoms such as 2-(2-naphthyl)vinyl and the like, and the like can be mentioned.

As the aromatic hydrocarbon group, an aromatic hydrocarbon group having 6 to 14 carbon atoms (e.g., an aryl group etc.) is preferable. As the aromatic hydrocarbon group, for example, phenyl, naphthyl, anthryl, phenanthryl, acenaphthylenyl, biphenylyl and the like can be mentioned, with preference given to phenyl, 1-naphthyl, 2-naphthyl and the like.

As the substituent for the "optionally substituted hydrocarbon group", for example, an aromatic heterocyclic group (e.g., thienyl, furyl, pyridyl, oxazolyl, thiazolyl and the like), a non-aromatic heterocyclic group (e.g., tetrahydrofuryl, morpholino, thiomorpholino, piperidino, pyrrolidinyl, piperazinyl and the like), an amino group, an amino group mono- or di-substituted by an alkyl group having 1 to 4 carbon atoms or an acyl group having 2 to 8 carbon atoms (e.g., an alkanoyl group and the like), an amidino group, an acyl group having 2 to 8 carbon atoms (e.g., an alkanoyl group and the like), a carbamoyl group, a carbamoyl group mono- or di-substituted by an alkyl group having 1 to 4 carbon atoms, a sulfamoyl group, a sulfamoyl group mono- or di-substituted by an alkyl group having 1 to 4 carbon atoms, a carboxyl group, an alkoxycarbonyl group having 2 to 8 carbon atoms, a hydroxy group, an alkoxy group having 1 to 6 carbon atoms, which is optionally substituted by 1 to 3 halogen atoms (e.g., fluorine, chlorine, bromine, iodine and the like), an alkenyloxy group having 2 to 5 carbon atoms, which is optionally substituted by 1 to 3 halogen atoms (e.g., fluorine, chlorine, bromine, iodine and the like), a cycloalkyloxy group having 3 to 7 carbon atoms, an aralkyloxy group having 7 to 9 carbon atoms, an aryloxy group having 6 to 14 carbon atoms (e.g., phenyloxy, naphthyloxy and the like), a thiol group, an alkylthio group having 1 to 6 carbon atoms, which is optionally substituted by 1 to 3 halogen atoms (e.g., fluorine, chlorine, bromine, iodine and the like), an aralkylthio group having 7 to 9 carbon atoms, an arylthio group having 6 to 14 carbon atoms (e.g., phenylthio, naphthylthio and the like), a sulfo group, a cyano group, an azide group, a nitro group, a nitroso group, a halogen atom (e.g., fluorine, chlorine, bromine, iodine), and the like can be mentioned. The number of substituents is, for example, 1 to 3.

As the aromatic heterocyclic group of the "optionally substituted aromatic heterocyclic group", for example, a monocyclic, bicyclic or tricyclic aromatic heterocyclic group containing, as ring-constituting atoms, besides carbon atoms, 1 to 5 heteroatoms selected from an oxygen atom, a sulfur atom and a nitrogen atom, and the like can be mentioned.

Preferable examples of the monocyclic aromatic heterocyclic group include furyl, thienyl, pyrrolyl, oxazolyl, isoxazolyl, thiazolyl, isothiazolyl, imidazolyl, pyrazolyl, oxadiazolyl (1,2,3-oxadiazolyl, 1,2,4-oxadiazolyl, 1,3,4-oxadiazolyl), furazanyl, thiadiazolyl (1,2,3-thiadiazolyl, 1,2,4-thiadiazolyl, 1,3,4-thiadiazolyl), triazolyl (1,2,3-triazolyl, 1,2,4-triazolyl), tetrazolyl, pyridyl, pyrimidinyl, pyridazinyl, pyrazinyl, triazinyl and the like.

Preferable examples of the bicyclic or tricyclic aromatic heterocyclic group include benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, α-carbonylyl, β-carbonylyl, γ-carbonylyl, acridinyl, phenoxazinyl, phenothiazinyl, phenazinyl, phenoxathiinyl, thianthrenyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

As the non-aromatic heterocyclic group of the "optionally substituted non-aromatic heterocyclic group", for example, a non-aromatic heterocyclic group having 2 to 10 carbon atoms containing, as ring-constituting atoms, besides carbon atoms, 1 to 3 heteroatoms selected from an oxygen atom, a sulfur atom and a nitrogen atom, and the like can be mentioned. Preferable examples of the non-aromatic heterocyclic group include oxiranyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidino, morpholino, thiomorpholino and the like.

As the substituent for the aforementioned "optionally substituted aromatic heterocyclic group" and "optionally substituted non-aromatic heterocyclic group", for example, an alkyl group having 1 to 6 carbon atoms, which is optionally substituted by 1 to 3 halogen atoms (e.g., fluorine, chlorine, bromine, iodine and the like), an alkenyl group having 2 to 6 carbon atoms, which is optionally substituted by 1 to 3 halogen atoms (e.g., fluorine, chlorine, bromine, iodine and the like), a cycloalkyl group having 3 to 7 carbon atoms, an aryl group having 6 to 14 carbon atoms (e.g., phenyl, naphthyl and the like), an aromatic heterocyclic group (e.g., thienyl, furyl, pyridyl, oxazolyl, thiazolyl and the like), a non-aromatic heterocyclic group (e.g., tetrahydrofuryl, morpholino, thiomorpholino, piperidino, pyrrolidinyl, piperazinyl and the like), an aralkyl group having 7 to 9 carbon atoms, an amino group, an amino group mono- or di-substituted by an alkyl group having 1 to 4 carbon atoms or an acyl group having 2 to 8 carbon atoms (e.g., an alkanoyl group and the like), an amidino group, an acyl group having 2 to 8 carbon atoms (e.g., an alkanoyl group and the like), a carbamoyl group, a carbamoyl group mono- or di-substituted by an alkyl group having 1 to 4 carbon atoms, a sulfamoyl group, a sulfamoyl group mono- or di-substituted by an alkyl group having 1 to 4 carbon atoms, a carboxyl group, an alkoxycarbonyl group having 2 to 8 carbon atoms, a hydroxy group, an alkoxy group having 1 to 6 carbon atoms, which is optionally substituted by 1 to 3 halogen atoms (e.g., fluorine, chlorine, bromine, iodine and the like), an alkenyloxy group having 2 to 5 carbon atoms, which is optionally substituted by 1 to 3 halogen atoms (e.g., fluorine, chlorine, bromine, iodine and the like), a cycloalkyloxy group having 3 to 7 carbon atoms, an aralkyloxy group having 7 to 9 carbon atoms, an aryloxy group having 6 to 14 carbon atoms (e.g., phenyloxy, naphthyloxy and the like), a thiol group, an alkylthio group having 1 to 6 carbon atoms, which is optionally substituted by 1 to 3 halogen-atoms (e.g., fluorine, chlorine, bromine, iodine and the like), an aralkylthio group having 7 to 9 carbon atoms, an arylthio group having 6 to 14 carbon atoms (e.g., phenylthio, naphthylthio and the like), a sulfo group, a cyano group, an azide group, a nitro group, a nitroso group, a halogen atom (e.g., fluorine, chlorine, bromine, iodine), and the like can be mentioned. The number of substituents is, for example, 1 to 3.

As the "acyl group", for example, an acyl group having 1 to 13 carbon atoms, specifically formyl as well as a group of the formula: $-COR^7$, $-SO_2R^7$, $-SOR^7$ or $-PO_3R^7R^8$, wherein $R^7$ and $R^8$ are the same or different and each is an optionally substituted hydrocarbon group or an optionally substituted aromatic heterocyclic group, and the like can be mentioned.

As the "optionally substituted hydrocarbon group" for $R^7$ or $R^8$, for example, those exemplified as the aforementioned substituent for $R^1$ and $R^2$ can be mentioned. The hydrocarbon group is preferably an alkyl group having 1 to 10 carbon atoms, an alkenyl group having 2 to 10 carbon atoms, a cycloalkyl group having 3 to 7 carbon atoms, a cycloalkenyl group having 5 to 7 carbon atoms or an aryl group having 6 to 14 carbon atoms.

As the "optionally substituted aromatic heterocyclic group" for $R^7$ or $R^8$, for example, those exemplified as the aforementioned substituent for R and $R^2$ can be mentioned. The aromatic heterocyclic group is preferably thienyl, furyl or pyridyl.

The substituent for the "optionally substituted hydrocarbon group" and the "optionally substituted aromatic heterocyclic group" for $R^7$ or $R^8$ is preferably a $C_{1-6}$ alkoxy group optionally substituted by 1 to 3 halogen atoms (e.g., fluorine, chlorine, bromine, iodine and the like), a halogen atom (e.g., fluorine, chlorine, bromine, iodine and the like), a nitro group, a hydroxy group or an amino group. The number of substituents is, for example, 1 to 3.

Preferable examples of the acyl group include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonoyl, 2-cyclohexenecarbonyl, benzoyl, nicotinoyl, isonicotinoyl and the like.

As the "optionally substituted amino group", for example, an amino group optionally mono- or di-substituted by an aliphatic hydrocarbon group having 1 to 10 carbon atoms, an alicyclic hydrocarbon group having 3 to 7 carbon atoms, an aromatic hydrocarbon group having 6 to 14 carbon atoms or an acyl group having 1 to 13 carbon atoms can be mentioned. As each of these groups, those exemplified as the aforementioned substituent for $R^1$ and $R^2$ can be mentioned. Moreover, the acyl group having 1 to 13 carbon atoms is preferably an alkanoyl group having 2 to 10 carbon atoms, an arylcarbonyl group having 7 to 13 carbon atoms, and the like.

Preferable examples of the substituted amino group include methylamino, dimethylamino, ethylamino, diethylamino, propylamino, dibutylamino, diallylamino, cyclohexylamino, acetylamino, propionylamino, benzoylamino, phenylamino, N-methyl-N-phenylamino and the like.

As the "optionally substituted hydroxy group", for example, a hydroxy group optionally substituted by an aliphatic hydrocarbon group having 1 to 10 carbon atoms, an alicyclic hydrocarbon group having 3 to 7 carbon atoms, an aromatic-aliphatic hydrocarbon group having 7 to 13 carbon atoms, an aromatic hydrocarbon group having 6 to 14 carbon atoms or an acyl group having 1 to 13 carbon atoms, each of which is optionally substituted, can be mentioned. As each of these groups, those exemplified as the aforementioned substituent for $R^1$ and $R^2$ can be mentioned.

As the substituent these groups may have, for example, a halogen atom (e.g., fluorine, chlorine, bromine, iodine and the like), a $C_{1-6}$ alkoxy group optionally substituted by 1 to 3 halogen atoms (e.g., fluorine, chlorine, bromine, iodine and the like), a hydroxy group, a nitro group, an amino group, and the like can be mentioned. The number of substituents is, for example, 1 or 2.

As the substituted hydroxy group, for example, an alkoxy group, an alkenyloxy group, a cycloalkyloxy group, a cycloalkenyloxy group, an aralkyloxy group, an aryloxy group and an acyloxy group, each of which is optionally substituted, and the like can be mentioned.

Preferable examples of the alkoxy group include an alkoxy group having 1 to 10 carbon atoms, such as methoxy, ethoxy, propoxy, isopropoxy, butoxy, isobutoxy, sec.-butoxy, t.-butoxy, pentyloxy, isopentyloxy, neopentyloxy, hexyloxy, heptyloxy, nonyloxy and the like.

Preferable examples of the alkenyloxy group include an alkenyloxy group having 2 to 10 carbon atoms, such as allyloxy, crotyloxy, 2-pentenyloxy, 3-hexenyloxy and the like.

Preferable examples of the cycloalkyloxy group include a cycloalkyloxy group having 3 to 7 carbon atoms, such as cyclobutoxy, cyclopentyloxy, cyclohexyloxy and the like.

Preferable examples of the cycloalkenyloxy group include a cycloalkenyloxy group having 5 to 7 carbon atoms, such as 2-cyclopentenyloxy, 2-cyclohexenyloxy and the like.

Preferable examples of the aralkyloxy group include an aralkyloxy group having 7 to 10 carbon atoms, such as phenyl-$C_{1-4}$ alkyloxy (e.g., benzyloxy, phenethyloxy and the like) and the like.

Preferable examples of the aryloxy group include an aryloxy group having 6 to 14 carbon atoms, such as phenoxy, naphthyloxy and the like.

Preferable examples of the acyloxy group include an acyloxy group having 2 to 13 carbon atoms, more preferably alkanoyloxy having 2 to 4 carbon atoms (e.g., acetyloxy, propionyloxy, butyryloxy, isobutyryloxy and the like) and the like.

The above-mentioned alkoxy group, alkenyloxy group, cycloalkyloxy group, cycloalkenyloxy group, aralkyloxy group, aryloxy group and acyloxy group may have 1 or 2 substituents at substitutable positions. As such substituent, for example, a halogen atom (e.g., fluorine, chlorine, bromine, iodine and the like), a $C_{1-6}$ alkoxy group optionally substituted by 1 to 3 halogen atoms (e.g., fluorine, chlorine, bromine, iodine and the like), a hydroxy group, a nitro group, an amino group, and the like can be mentioned.

As the optionally substituted thiol group, for example, a thiol group optionally substituted by an aliphatic hydrocarbon group having 1 to 10 carbon atoms, an alicyclic hydrocarbon group having 3 to 7 carbon atoms, an aromatic-aliphatic hydrocarbon group having 7 to 13 carbon atoms, an aromatic hydrocarbon group having 6 to 14 carbon atoms, an acyl group, having 1 to 13 carbon atoms or a heteroaryl group can be mentioned. As each of these groups, those exemplified as the aforementioned substituent for $R^1$ and $R^2$ can be mentioned.

Preferable examples of the heteroaryl group include pyridyl (e.g., 2-pyridyl, 3-pyridyl), imidazolyl (e.g., 2-imidazolyl), triazolyl (e.g., 1,2,4-triazol-5-yl) and the like.

As the substituted thiol group, for example, an alkylthio group, a cycloalkylthio group, an aralkylthio group, an arylthio group, an acylthio group, a heteroarylthio group, and the like can be mentioned.

Preferable examples of the alkylthio group include an alkylthio group having 1 to 10 carbon atoms, such as methylthio, ethylthio, propylthio, isopropylthio, butylthio, isobutylthio, sec.-butylthio, t.-butylthio, pentylthio, isopentylthio, neopentylthio, hexylthio, heptylthio, nonylthio and the like.

Preferable examples of the cycloalkylthio group include a cycloalkylthio group having 3 to 7 carbon atoms, such as cyclobutylthio, cyclopentylthio, cyclohexylthio and the like.

Preferable examples of the aralkylthio group include an aralkylthio group having 7 to 10 carbon atoms, such as phenyl-$C_{1-4}$ alkylthio (e.g., benzylthio, phenethylthio and the like) and the like.

Preferable examples of the arylthio group include an arylthio group having 6 to 14 carbon atoms, such as phenylthio, naphthylthio and the like.

Preferable examples of the acylthio group include an acylthio group having 2 to 13 carbon atoms, more preferably an alkanoylthio group having 2 to 4 carbon atoms (e.g., acetylthio, propionylthio, butyrylthio, isobutyrylthio and the like) and the like.

Preferable examples of the heteroarylthio group include pyridylthio (e.g., 2-pyridylthio, 3-pyridylthio), imidazolylthio (e.g., 2-imidazolylthio), triazolylthio (e.g., 1,2,4-triazol-5-ylthio) and the like.

For the optionally esterified carboxyl group, the esterified carboxyl group is, for example, an alkoxycarbonyl group having 2 to 5 carbon atoms (e.g., methoxycarbonyl, ethoxycarbonyl, propoxycarbonyl, butoxycarbonyl and the like), an aralkyloxycarbonyl group having 8 to 10 carbon atoms (e.g., benzyloxycarbonyl and the like), an aryloxycarbonyl group having 7 to 15 carbon atoms optionally substituted by 1 or 2 alkyl groups having 1 to 3 carbon atoms, such as phenoxycarbonyl, p-tolyloxycarbonyl and the like, and the like.

For the optionally amidated carboxyl group, the amidated carboxyl group is a group of the formula:

wherein $R^9$ and $R^{10}$ are the same or different and each is a hydrogen atom, an optionally substituted hydrocarbon group or an optionally substituted heterocyclic group.

Here, as the "optionally substituted hydrocarbon group" for $R^9$ or $R^{10}$, those exemplified as the aforementioned substituent for $R^1$ or $R^2$ can be mentioned. As the "optionally substituted heterocyclic group" for $R^9$ and $R^{10}$, moreover, the "optionally substituted aromatic heterocyclic group" and the "optionally substituted non-aromatic heterocyclic group" exemplified as the aforementioned substituent for $R^1$ or $R^2$ can be mentioned.

The substituent of the hydrocarbon group and the heterocyclic group is preferably a halogen atom (e.g., fluorine, chlorine, bromine, iodine and the like), a $C_{1-6}$ alkoxy group optionally substituted by 1 to 3 halogen atoms (e.g., fluorine, chlorine, bromine, iodine and the like), a nitro group, a hydroxy group or an amino group. The number of substituents is, for example, 1 to 3.

As the "optionally substituted hydrocarbon group" for $R^1$ and $R^2$, those exemplified as the substituent for the aforementioned "monocyclic aromatic hydrocarbon group" for $R^1$ or $R^2$ and the like can be mentioned.

The "optionally substituted hydrocarbon group" is preferably an alkyl group having 1 to 4 carbon atoms (e.g., methyl).

As the halogen atom for $R^1$ and $R^2$, for example, fluorine, chlorine, bromine, iodine and the like, can be mentioned. Of these, chlorine is preferable.

In the formulas (I), (I-1), (I-2), (I-3) and the like, one of $R^1$ and $R^2$ (preferably $R^2$) is preferably an optionally substituted monocyclic aromatic hydrocarbon group, and the other (preferably $R^1$) is preferably a hydrogen atom, a halogen atom or an optionally substituted hydrocarbon group.

As used herein, the "optionally substituted monocyclic aromatic hydrocarbon group" is preferably a phenyl group optionally having 1 to 3 substituents selected from a halogen atom (e.g., fluorine, chlorine, bromine, iodine and the like); an optionally halogenated $C_{1-6}$ alkyl group (e.g., trifluoromethyl, t.-butyl); a nitro group; an amino group; a $C_{6-14}$ aryloxy group (e.g., phenoxy) and the like.

In addition, the "halogen atom" is preferably chlorine and the "optionally substituted hydrocarbon group" is preferably an alkyl group having 1 to 4 carbon atoms (e.g., methyl).

In the formulas (I-1), (I-2) and (I-3), $R^1$ is preferably a hydrogen atom or an, alkyl group having 1 to 4 carbon atoms (e.g., methyl) and $R^2$ is preferably a phenyl group optionally substituted by an optionally halogenated $C_{1-6}$ alkyl group (e.g., trifluoromethyl, t.-butyl).

In the formula (I-1), $R^2$ is more preferably a phenyl group substituted by a halogenated $C_{1-6}$ alkyl group (e.g., trifluoromethyl).

In the formula (I-3), as the "optionally substituted hydrocarbon group" for R, those exemplified as the aforementioned substituent for the "monocyclic aromatic hydrocarbon group" for $R^1$ or $R^2$ and the like can be mentioned.

The "optionally substituted hydrocarbon group" is preferably an alkyl group having 1 to 4 carbon atoms (e.g., methyl).

As the "5- or 6-membered heterocycle (except 1,3-azole)" for B, for example, a 5- or 6-membered heterocycle (except 1,3-azole) containing, as ring-constituting atoms, besides carbon atoms, 1 to 4 heteroatoms selected from an oxygen atom, a sulfur atom and a nitrogen atom can be mentioned.

Preferable examples of the 5- or 6-membered heterocycle include a 5-membered aromatic heterocycle, such as furan, thiophene, pyrrole, isoxazole, isothiazole, pyrazole, oxadiazole (1,2,3-oxadiazole, 1,2,4-oxadiazole, 1,3,4-oxadiazole), furazan, thiadiazole (1,2,3-thiadiazole, 1,2,4-thiadiazole, 1,3,4-thiadiazole), triazole (1,2,3-triazole, 1,2,4-triazole), tetrazole and the like;

a 6-membered aromatic heterocycle, such as pyridine, pyrimidine, pyridazine, pyrazine, triazine and the like;

a 5-membered non-aromatic heterocycle, such as pyrrolidine, imidazolidine, pyrazolidine, tetrahydrofuran, pyrroline, imidazoline, pyrazoline and the like;

a 6-membered non-aromatic heterocycle, such as morpholin, thiomorpholine, piperazine, pyrrolidinyl, piperidine, tetrahydropyran and the like; and the like.

B is preferably a 5- or 6-membered aromatic heterocycle, more preferably, furan, thiophene, pyrrole, isoxazole, oxadiazole, triazole, pyridine and the like.

As the "aromatic hydrocarbon group" of the "optionally substituted aromatic hydrocarbon group" for A, for example, those exemplified as the aforementioned hydrocarbon group for the "optionally substituted hydrocarbon group", which is the substituent for $R^1$ and $R^2$ can be mentioned.

As the substituent for the "optionally substituted aromatic hydrocarbon group", for example, those exemplified as the aforementioned substituent for the "optionally substituted hydrocarbon group", which is the substituent for $R^1$ and $R^2$ can be mentioned. The number of substituents is, for example, 1 to 3.

As the "optionally substituted aromatic heterocyclic group" for A, for example, those exemplified as the aforementioned substituent for $R^1$ and $R^2$ can be mentioned. The number of substituents is, for example, 1 to 3.

The substituent for the "optionally substituted aromatic hydrocarbon group" and the "optionally substituted aromatic heterocyclic group" for A is preferably a hydroxy group; an aralkyloxy group having 7 to 9 carbon atoms (e.g., benzyloxy); an amino group; an amino group mono- or di-substituted by an alkyl group having 1 to 4 carbon atoms or an acyl group having 2 to 8 carbon atoms (e.g., trifluoroacetyl); a nitro group; a halogen atom; an alkyl group having 1 to 6 carbon atoms, which is optionally substituted by 1 to 3 halogen atoms; an alkoxy group having 1 to 6 carbon atoms, which is optionally substituted by 1 to 3 halogen atoms; and the like.

A is preferably an optionally substituted aromatic hydrocarbon group, more preferably an aryl group having 6 to 14 carbon atoms (e.g., phenyl, naphthyl and the like), which optionally has 1 to 3 substituents selected from a hydroxy group; an aralkyloxy group having 7 to 9 carbon atoms (e.g., benzyloxy); an amino group; an amino group mono- or di-substituted by an alkyl group having 1 to 4 carbon atoms or an acyl group having 2 to 8 carbon atoms (e.g., trifluoroacetyl); a nitro group; a halogen atom; an alkyl group having 1 to 6 carbon atoms optionally substituted by 1 to 3 halogen atoms; and alkoxy group having 1 to 6 carbon atoms, which is optionally substituted by 1 to 3 halogen atoms, particularly preferably an aryl group having 6 to 14 carbon atoms (e.g., phenyl, naphthyl and the like).

In the formula (I-2), $A_1$ is as defined for the aforementioned A except that it is free of an optionally esterified carboxyl group as a substituent.

$R^3$ is a hydrogen atom, $-OR^4$ ($R^4$ is a hydrogen atom or an optionally substituted hydrocarbon group) or $-NR^5R^6$ ($R^5$ and $R^6$ are the same or different and each is a hydrogen atom or an optionally substituted hydrocarbon group, or $R^5$ and $R^6$ may form an optionally substituted ring together with the adjacent nitrogen atom).

As the "optionally substituted hydrocarbon group" for $R^4$, those exemplified as the aforementioned substituent for $R^1$ and $R^2$ can be mentioned.

The "optionally substituted hydrocarbon group" is preferably an "alkyl group having 1 to 4 carbon atoms (preferably, methyl, ethyl)", an "aralkyl group having 7 to 13 carbon atoms (preferably, benzyl)" and the like.

As the "optionally substituted hydrocarbon group" for $R^5$ or $R^6$, those exemplified as the aforementioned substituent for $R^1$ and $R^2$ can be mentioned.

As the ring of the "optionally substituted ring" formed by $R^5$ and $R^6$ together with the adjacent nitrogen atom, for example, a 5- to 7-membered nitrogen-containing heterocycle can be mentioned. Preferable examples of the 5- to 7-membered nitrogen-containing heterocycle include pyrrolidine, piperidine, hexamethylenimine, morpholine, thiomorpholine, piperazine and the like.

As the substituent for the "optionally substituted ring", for example, those exemplified as the aforementioned substituent for the "optionally substituted aromatic heterocyclic group", which is the substituent for $R^1$ and $R^2$ can be mentioned.

$R^3$ is preferably a hydrogen atom or $-OR^4$ (the symbol is as defined above), and more preferably $-OR^4$ (the symbol is as defined above).

As used herein, $R^4$ is preferably a hydrogen atom or an alkyl group having 1 to 4 carbon atoms (e.g., methyl, ethyl).

In the formula (I-1), the optionally substituted monocyclic aromatic hydrocarbon group and the optionally substituted hydrocarbon group for $R^1$ or $R^2$ are not a 3,4-dimethoxyphenyl group, a 4-pentyloxyphenyl group and a phenyl group substituted by an optionally alkyl-esterified carboxyl group.

In the formula (I-2), the optionally substituted monocyclic aromatic hydrocarbon group and the optionally substituted hydrocarbon group for $R^1$ or $R^2$ are not a phenyl group optionally having a substituent at the 4-position and a phenyl group substituted by an optionally alkyl-esterified carboxyl group; and the optionally substituted monocyclic aromatic heterocyclic group containing one heteroatom for $R^1$ or $R^2$ is not a substituted thienyl group.

In the formula (I-3), when one of $R^1$ and $R^2$ is an optionally substituted phenyl group, then the other should not be pyridyl.

Preferable examples of the compound represented by the formula (I) include the following compound.

A compound wherein
one of $R^1$ and $R^2$ (preferably $R^2$) is a phenyl group optionally having 1 to 3 substituents selected from a halogen atom (preferably chlorine); an optionally halogenated $C_{1-6}$ alkyl group (preferably trifluoromethyl, t.-butyl); a nitro group; an amino group; and a $C_{6-14}$ aryloxy group (preferably phenoxy), and the other (preferably $R^1$) is a hydrogen atom, a halogen atom (preferably chlorine) or an alkyl group having 1 to 4 carbon atoms (preferably methyl);

B is furan, thiophene, pyrrole, isoxazole, oxadiazole, triazole or pyridine (preferably furan, thiophene, pyrrole);

A is an aryl group having 6 to 14 carbon atoms (preferably phenyl), which optionally has 1 to 3 substituents selected from a hydroxy group; an aralkyloxy group having 7 to 9 carbon atoms (preferably benzyloxy); an amino group; an amino group mono- or di-substituted by an alkyl group having 1 to 4 carbon atoms or an acyl group having 2 to 8 carbon atoms (preferably trifluoroacetyl); a nitro group; a halogen atom; an alkyl group having 1 to 6 carbon atoms, which is optionally substituted by 1 to 3 halogen atoms; and an alkoxy group having 1 to 6 carbon atoms, which is optionally substituted by 1 to 3 halogen atoms; and $R^3$ is a hydrogen atom or —$OR^4$, and $R^4$ is a hydrogen atom or an alkyl group having 1 to 4 carbon atoms (preferably methyl, ethyl).

The salt of a compound of the formula (I) (hereinafter also referred to as Compound (I)) is preferably a pharmacologically acceptable salt, and is exemplified by salts with inorganic bases, salts with organic bases, salts with inorganic acids, salts with organic acids, and salts with basic or acidic amino acids, and the like.

Preferable examples of the salts with inorganic bases include alkali metal salts such as lithium salts, sodium salts and potassium salts; alkaline earth metal salts such as calcium salts and magnesium salts; aluminum salts and ammonium salts; and the like.

Preferable examples of the salts with organic bases include salts with trimethylamine, triethylamine, pyridine, picoline, ethanolamine, diethanolamine, triethanolamine, dicyclohexylamine, N,N-dibenzylethylenediamine and the like.

Preferable examples of the salts with inorganic acids include salts with hydrochloric acid, hydrobromic acid, nitric acid, sulfuric acid, phosphoric acid and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with basic amino acids include salts with arginine, lysine, ornithine and the like.

Preferable examples of the salts with acidic amino acids include salts with aspartic acid, glutamic acid and the like.

As the salts of the compounds represented by the formulas (I-1), (I-2), (I-3) and the like, those similar to the salts of Compound (I) can be mentioned.

Compound (I) may be used as a prodrug. A prodrug of Compound (I) refers to a compound capable of being converted to Compound (I) by reactions due to an enzyme, gastric juice and the like, under physiological conditions in vivo, i.e., a compound capable of being converted to Compound (I) upon enzymatic oxidation, reduction, hydrolysis and the like, or a compound capable of being converted to Compound (I) upon hydrolysis and the like by gastric juice and the like. Examples of the prodrugs of Compound (I) include compounds derived by acylation, alkylation or phosphorylation of the amino group in Compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, tetrahydropyranylation, pyrrolidylmethylation, pivaloyloxymethylation or tert-butylation of the amino group in Compound (I), etc.); compounds derived by acylation, alkylation, phosphorylation or boration of the hydroxy group in Compound (I) (e.g., compounds derived by acetylation, palmitoylation, propanoylation, pivaloylation, succinylation, fumarylation, alanylation, dimethylaminomethylcarbonylation or tetrahydropyranylation of the hydroxy group in Compound (I), etc.); compounds derived by esterification or amidation of the carboxyl group in Compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation of the carboxyl group in Compound (I), etc.), and the like. These compounds can be produced from Compound (I) by methods known per se.

The prodrug of Compound (I) may be one capable of being converted to Compound (I) under physiological conditions, as described in "Iyakuhin No Kaihatsu (Development of Drugs)", vol. 7, Molecular Designing, published by Hirokawa Shoten, 1990, pages 163–198.

In addition, Compound (I) may be labeled with an isotope (e.g., $^3H$, $^{14}C$, $^{35}S$, $^{125}I$ etc.).

Moreover, Compound (I) may be an anhydride or a hydrate.

The compounds represented by the formulas (I-1), (I-2), (I-3) and the like can be also used as a prodrug like Compound (I), may be labeled with an isotope (e.g., $^3H$, $^{14}C$, $^{35}S$, $^{125}I$ and the like) and the like, and may be an anhydride or a hydrate.

Compound (I) [inclusive of Compounds (I-1), (I-2), (I-3)] and salts thereof (hereinafter sometimes to be simply abbreviated as the compound of the present invention) show low toxicity and can be used as they are or in the form of a pharmaceutical composition obtainable by admixing with a pharmacologically acceptable carrier and the like, as a retinoid-related receptor (except retinoic acid receptors) function regulating agent, to mammals (e.g., human, mouse, rat, rabbit, dog, cat, bovine, horse, swine, monkey etc.).

Here, the pharmacologically acceptable carriers are exemplified by various organic or inorganic carrier substances in common use as materials for pharmaceutical preparations, and they are formulated as excipients, lubricants, binders, and disintegrants for solid preparations; solvents, solubilizers, suspending agents, isotonizing agents, buffers, soothing agents for liquid preparations; etc. In addition, other additives for pharmaceutical preparations, such as antiseptics, antioxidants, coloring agents, and sweetening agents, may be also used as necessary.

Preferable examples of the excipients include lactose, saccharose, D-mannitol, D-sorbitol, starch, gelatinized starch, crystalline cellulose, low-substituted hydroxypropylcellulose, carboxymethylcellulose sodium, gum arabic, dextrin, pullulan, light silicic anhydride, synthetic aluminum silicate, magnesium metasilicate aluminate and the like.

Preferable examples of the lubricants include magnesium stearate, calcium stearate, talc, colloidal silica and the like.

Preferable examples of the binders include gelatinized starch, sucrose, gelatin, gum arabic, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like.

Preferable examples of the disintegrants include lactose, saccharose, starch, carboxymethylcellulose, carboxymethylcellulose calcium, croscarmellose sodium, carboxymethyl starch sodium, light silicic anhydride, low-substituted hydroxypropylcellulose and the like.

Preferable examples of the solvents include water for injection, physiological saline, Ringer's solution, alcohol, propylene glycol, polyethylene glycol, sesame oil, corn oil, olive oil, cottonseed oil and the like.

Preferable examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of the suspending agents include surfactants such as stearyltriethanolamine, sodium lauryl sulfate, laurylaminopropionic acid, lecithin, benzalkonium chloride, benzethonium chloride, monostearic glycerol and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, polyoxyethylene hydrogenated castor oil and the like.

Preferable examples of the isotonizing agents include sodium chloride, glycerol, D-mannitol, D-sorbitol, glucose and the like, and the like.

Preferable examples of the buffers include buffer solutions of phosphates, acetates, carbonates, citrates and the like.

Preferable examples of the soothing agents include benzyl alcohol and the like.

Preferable examples of the antiseptics include p-oxybenzoic acid esters, chlorobutanol, benzyl alcohol, phenethyl alcohol, dehydroacetic acid, sorbic acid and the like.

Preferable examples of the antioxidants include sulfites, ascorbates and the like.

Preferable examples of the coloring agents include water-soluble tar colors for food (e.g., food colors such as Food Color Red Nos. 2 and 3, Food Color Yellow Nos. 4 and 5, Food Color Blue Nos. 1 and 2 etc.), water-insoluble lake colors (e.g., aluminum salts of the aforementioned water-soluble tar colors for food etc.), natural colors (e.g., β-carotene, chlorophyll, red iron oxide etc.), and the like.

Preferable examples of the sweetening agents include saccharin sodium, dipotassium glycyrrhetinate, aspartame, stevia and the like.

Examples of the dosage forms of the pharmaceutical composition include oral preparations such as tablets (including sublingual tablets and orally disintegrating tablets), capsules (including soft capsules and microcapsules), granules, powders, troches, syrups, emulsions, suspensions and the like; and parenteral preparations such as injections (e.g., subcutaneous injections, intravenous injections, intramuscular injections, intraperitoneal injections and the like), external preparations (e.g., preparations for nasal administration, dermal preparations, ointments and the like), suppositories (e.g., rectal suppositories, vaginal suppositories and the like), pellets, drip infusions, eye drops, transpulmonary agents (inhalant) and the like. Each of these preparations can be orally or parenterally administered safely. In addition, these preparations may be a controlled-release preparation such as a rapid release preparation, a sustained-release preparation and the like (e.g., sustained-release microcapsules and the like).

The pharmaceutical composition can be prepared according to conventional methods in the fields of pharmaceutical manufacturing techniques, such as the methods described in the Japanese Pharmacopoeia and the like. Specific production methods for the preparations are hereinafter described in detail.

An oral preparation, for instance, is produced by adding to the active ingredient, for example, an excipient (e.g., lactose, saccharose, starch, D-mannitol etc.), a disintegrant (e.g., carboxymethylcellulose calcium etc.), a binder (e.g., gelatinized starch, gum arabic, carboxymethylcellulose, hydroxypropylcellulose, polyvinylpyrrolidone etc.) or a lubricant (e.g., talc, magnesium stearate, polyethyleneglycol 6000 etc.) and the like, compression molding the obtained mixture, and, if necessary, coating by a method known per se using a coating base for the purpose of taste masking, enteric coating or sustained release.

Examples of the coating base include a sugar coating base, a water-soluble film coating base, an enteric film coating base, a sustained-release film coating base and the like.

As the sugar coating base, saccharose is employed. Further, one or more kinds selected from talc, precipitated calcium carbonate, gelatin, gum arabic, pullulan, carnauba wax and the like may be used in combination.

Examples of the water-soluble film coating base include cellulose polymers such as hydroxypropylcellulose, hydroxypropylmethylcellulose, hydroxyethylcellulose, methylhydroxyethylcellulose; synthetic polymers such as polyvinylacetal diethylaminoacetate, aminoalkyl methacrylate copolymer E [Eudragit E (trademark), Rhom Pharma] and polyvinylpyrrolidone; and polysaccharides such as pullulan, and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate; acrylic acid polymers such as methacrylic acid copolymer L [Eudragit L (trademark), Rhom Pharma], methacrylic acid copolymer LD [Eudragit L-30D55 (trademark), Rhom Pharma], methacrylic acid copolymer S [Eudragit S (trademark), Rhom Pharma]; natural products such as shellac, and the like.

Examples of the sustained-release film coating base include cellulose polymers such as ethylcellulose; acrylic acid polymers such as aminoalkyl methacrylate copolymer RS [Eudragit RS (trademark), Rhom Pharma] and an ethyl acrylate-methyl methacrylate copolymer suspension [Eudragit NE (trademark), Rhom Pharma] and the like.

Two or more of the above coating bases may be used in admixture in an appropriate ratio. For coating, a shading agent such as titanium oxide, red ferric oxide and the like may be used.

Injections are produced by dissolving, suspending or emulsifying the active ingredient in an aqueous solvent (e.g., distilled water, physiological saline, Ringer's solution etc.) or an oleaginous solvent (e.g., vegetable oils such as olive oil, sesame oil, cotton seed oil, corn oil; propylene glycol, etc.) and the like, together with a dispersant (e.g., polysorbate 80, polyoxyethylene hydrogenated castor oil 60, polyethylene glycol, carboxymethylcellulose, sodium alginate etc.), a preservative (e.g., methylparaben, propylparaben, benzyl alcohol, chlorobutanol, phenol etc.), an isotonizing agent (e.g., sodium chloride, glycerol, D-mannitol, D-sorbitol, glucose etc.) and the like. On such occasions, if desirable, additives such as a solubilizer (e.g., sodium salicylate, sodium acetate etc.), a stabilizer (e.g., human serum albumin etc.), a soothing agent (e.g., benzyl alcohol etc.) and the like, may be used.

The compound of the present invention has a glucose-lowering action, a lipid-lowering action, a blood insulin lowering action, an insulin resistance improving action, an insulin sensitizing action and a retinoid-related receptor (except retinoic acid receptors) function regulating activity.

As used herein, the function regulating activity refers to the activation or inhibition of the function (i.e., transduction) of retinoid-related receptors (except retinoic acid receptors).

The term "retinoid-related receptor" used here is classified as a nuclear receptor, and is a DNA-binding transcription factor whose ligand is a signal molecule such as fat-soluble vitamins etc., and may be any of a monomer receptor, a homodimer receptor and a heterodimer receptor.

Here, examples of the monomer receptor include retinoid O receptor (hereinafter also abbreviated as ROR) α (GenBank Accession No. L14611), ROR β (GenBank Accession No. L14160), ROR γ (GenBank Accession No. U16997); Rev-erb α (GenBank Accession No. M24898), Rev-erb β (GenBank Accession No. L31785); ERRα (GenBank Accession No. X51416), ERRβ (GenBank Accession No. X51417); Ftz-FIα (GenBank Accession No. S65876), Ftz-FI β (GenBank Accession No. M81385); TIx (GenBank Accession No. S77482); GCNF (GenBank Accession No. U14666) and the like.

Examples of the homodimer receptor include homodimers formed by retinoid X receptor (hereinafter also abbreviated as RXR) α (GenBank Accession No. X52773), RXRβ (GenBank Accession No. M84820), RXRγ (GenBank Accession No. U38480); COUPα (GenBank Accession No. X12795), COUPβ (GenBank Accession No. M64497), COUPγ (GenBank Accession No. X12794); TR2α (GenBank Accession No. M29960), TR2β (GenBank Accession No. L27586); or HNF4α (GenBank Accession No. X76930), HNF4γ (GenBank Accession No. Z49826) and the like.

Examples of the heterodimer receptor include heterodimers which are formed by the above-mentioned retinoid X receptor (RXRα, RXRβ or RXRγ) and one receptor selected from thyroid hormone receptor (hereinafter also abbreviated as TR) α (GenBank Accession No. M24748), TRβ (GenBank Accession No. M26747); vitamin D receptor (VDR) (GenBank Accession No. J03258); peroxisome proliferator-activated receptor (hereinafter also abbreviated as PPAR) α (GenBank Accession No. L02932), PPARβ (PPARδ) (GenBank Accession No. U10375), PPARγ (GenBank Accession No. L40904); LXRα (GenBank Accession No. U22662), LXRβ (GenBank Accession No. U14534); FXR (GenBank Accession No. U18374); MB67 (GenBank Accession No. L29263); ONR (GenBank Accession No. X75163); and NURα (GenBank Accession No. L13740), NURβ (GenBank Accession No. X75918) and NURγ (GenBank Accession No. U12767).

The compound of the present invention has an excellent function activating action, in particular, for retinoid X receptors (RXRα, RXRβ, RXRγ) and peroxisome proliferator-activated receptors (PPARα, PPARβ (PPARδ), PPARγ), among the above-mentioned retinoid-related receptors, and is useful as a function activating agent for these receptors.

Further, the compound of the present invention has an excellent function activating action for peroxisome proliferator-activated receptors in heterodimer receptors formed from a retinoid X receptor and a peroxisome proliferator-activated receptor (e.g., heterodimer receptors formed from RXRα and PPARδ, heterodimer receptors formed from RXRα and PPARγ, etc.).

The compound of the present invention promotes transcriptional activity of these receptors without binding with a retinoid-related receptor (except retinoic acid receptors), particularly a peroxisome proliferator-activated receptor (preferably PPARγ). Therefore, the compound of the present invention is useful as a superior pharmaceutical agent (e.g., an agent for the prophylaxis or treatment of diabetes mellitus, hyperlipidemia etc., and the like) free of a body weight increase action, as compared to PPARγ ligand represented by an agent for improving insulin resistance and the like to be described below as a concomitant drug.

The compound of the present invention also has an enhancing effect on the PPARγ transcriptional activity that PPARγ ligand represented by an agent for improving insulin resistance and the like has. Therefore, use of the compound of the present invention and PPARγ ligand represented by an agent for improving insulin resistance and the like in combination affords a more superior glucose-lowering effect or a prophylactic or therapeutic effect on diabetes mellitus.

The compound of the present invention can be used as, for example, an agent for the prophylaxis or treatment of diabetes mellitus (e.g., type I diabetes mellitus, type II diabetes mellitus, gestational diabetes mellitus, etc.); an agent for the prophylaxis or treatment of hyperlipidemia (e.g., hypertriglyceridemia, hypercholesterolemia, hypo-high-density-lipoproteinemia, postprandial hyperlipemia etc.); an agent for improving insulin resistance; an insulin sensitizer; an agent for the prophylaxis or treatment of impaired glucose tolerance (IGT); and an agent for preventing progress from impaired glucose tolerance to diabetes mellitus.

Regarding diagnostic criteria of diabetes mellitus, new diagnostic criteria were reported by the Japan Diabetes Society in 1999.

According to this report, diabetes mellitus is a condition wherein the fasting blood glucose level (glucose concentration in venous plasma) is not less than 126 mg/dl, the 2-hour value (glucose concentration in venous plasma) of the 75 g oral glucose tolerance test (75 g OGTT) is not less than 200 mg/dl or the casual blood glucose level (glucose concentration in venous plasma) is not less than 200 mg/dl. In addition, a condition that does not fall within the scope of the above definition of diabetes mellitus, and which is not a "condition wherein the fasting blood glucose level (glucose concentration in venous plasma) is less than 110 mg/dl or the 2-hour value (glucose concentration in venous plasma) of the 75 g oral glucose tolerance test (75 g OGTT) is less than 140 mg/dl" (normal type), is called the "borderline type".

As regards the diagnostic criteria for diabetes mellitus, moreover, new diagnostic criteria were reported by ADA (American Diabetes Association) in 1997 and by WHO in 1998.

According to these reports, diabetes mellitus is a condition where the fasting blood glucose level (glucose concentration in venous plasma) is not less than 126 mg/dl, and the 2-hour value (glucose concentration in venous plasma) of the 75 g oral glucose tolerance test is not less than 200 mg/dl.

In addition, according to the above reports, impaired glucose tolerance is a condition where the fasting blood glucose level (glucose concentration in venous plasma) is less than 126 mg/dl, and the 2-hour value (glucose concentration in venous plasma) of the 75 g oral glucose tolerance test is not less than 140 mg/dl and less than 200 mg/dl. Furthermore, according to the ADA report, a condition where the fasting blood glucose level (glucose concentration in venous plasma) is not less than 110 mg/dl and less than 126 mg/dl, is called IFG (impaired fasting glucose). On the other hand, according to the WHO report, a condition of IFG (impaired fasting glucose) as such, where the 2-hour value (glucose concentration in venous plasma) of the 75 g oral glucose tolerance test is less than 140 mg/dl, is called IFG (impaired fasting glycemia).

The compound of the present invention can also be used as an agent for the prophylaxis or treatment of diabetes mellitus, borderline type, impaired glucose tolerance, IFG (impaired fasting glucose) and IFG (impaired fasting glycemia) as defined by the foregoing new diagnostic criteria. Furthermore, the compound of the present invention can be also used to prevent the progression of the borderline type, impaired glucose tolerance, IFG (impaired fasting glucose) or IFG (impaired fasting glycemia) to diabetes mellitus.

The compound of the present invention can be also used as an agent for the prophylaxis or treatment of, for example, diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, skin and soft tissue infection, lower limb infection etc.), diabetic gangrene, xerostomia, lowered sense of hearing, cerebrovascular disease, peripheral circulatory disturbance etc.), obesity, osteoporosis, cachexia (e.g., cancer cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, end-stage renal disease etc.), muscular dystrophy, myocardial infarction, angina pectoris, cerebrovascular disease (e.g., cerebral infarction, cerebral apoplexy), insulin resistant syndrome, syndrome X, hyperinsulinemia, hyperinsulinemia-induced sensory disorder, tumor (e.g., leukemia, breast cancer, prostate cancer, skin cancer etc.), irritable bowel syndrome, acute or chronic diarrhea, inflammatory diseases (e.g., Alzheimer's disease, rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, pancreatitis, inflammatory colitis, ulcerative colitis, etc.), visceral obesity syndrome and the like.

The compound of the present invention possesses a total cholesterol lowering action and enhances a plasma anti-atherogenic index [(HDL cholesterol/total cholesterol)× 100], and therefore, can be used as an agent for the prophylaxis or treatment of arteriosclerosis (e.g., atherosclerosis etc.) and the like.

Also, the compound of the present invention can be used for ameliorating bellyache, nausea, vomiting or dysphoria in epigastrium and the like, each of which is accompanied by peptic ulcer, acute or chronic gastritis, biliary dyskinesia, cholecystitis and the like, etc.

The compound of the present invention has a TNF-α inhibitory effect (TNF-α production amount lowering effect and a TNF-α activity lowering effect in organic tissue) and is also used as an agent for the prophylaxis or treatment of inflammatory diseases in which TNF-α is involved. Examples of such inflammatory diseases include diabetic complications (e.g., retinopathy, nephropathy, neuropathy, macroangiopathy etc.), rheumatoid arthritis, spondylitis deformans, osteoarthritis, lumbago, gout, postoperative or traumatic inflammation, remission of swelling, neuralgia, pharyngolaryngitis, cystitis, hepatitis, pneumonia, gastric mucosal injury (including aspirin-induced gastric mucosal injury) and the like.

The compound of the present invention has an apoptosis inhibitory activity, and can be used as an agent for the prophylaxis or treatment of diseases mediated by promotion of apoptosis. Examples of the diseases mediated by promotion of apoptosis include viral diseases (e.g., AIDS, fulminant hepatitis etc.), neurodegenerative diseases (e.g., Alzheimer's disease, Parkinson's disease, amyotrophic lateral sclerosis, retinitis pigmentosa, cerebellar degeneration etc.), myelodysplasia (e.g., aplastic anemia etc.), ischemic diseases (e.g., myocardial infarction, cerebral apoplexy etc.), hepatic diseases (e.g., alcoholic hepatitis, hepatitis B, hepatitis C etc.), joint-diseases (e.g., osteoarthritis etc.), atherosclerosis and the like.

The compound of the present invention can be used for reducing visceral fats, inhibiting accumulation of visceral fats, ameliorating glycometabolism, ameliorating lipid metabolism, ameliorating insulin resistance, inhibiting oxidized LDL production, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism, and the like.

The compound of the present invention can be used for secondary prevention and for inhibition of progress of the various diseases described above (e.g., cardiovascular events such as myocardial infarction etc.).

Although the dose of the compound of the present invention varies depending on the administration subject, the administration route, the target disease, the clinical conditions etc., it is desirable that the compound of the present invention be administered at a usual dosage per administration of about 0.005 to 50 mg/kg body weight, preferably 0.01 to 10 mg/kg body weight, more preferably 0.1 to 2 mg/kg body weight, 1 to 3 times a day, for oral administration to an adult diabetic patient, for instance.

The compound of the present invention can be used in combination with a drug such as a therapeutic agent for diabetes mellitus, a therapeutic agent for diabetic complications, an antihyperlipidemic agent, a hypotensive agent, an antiobesity agent, a diuretic agent, a chemotherapeutic agent, an immunotherapeutic agent, antithrombotic agent, a cachexia improving agent etc. (hereinafter, abbreviated as a concomitant drug). On such occasions, the timing of administration of the compound of the present invention and that of the concomitant drug are not limited. They may be administered simultaneously or in a staggered manner to the administration subject.

The concomitant drug may be a compound having a low molecular weight, or may be a protein, a polypeptide or an antibody, each of which has a high molecular weight, or may be a vaccine and the like. The dose of the concomitant drug can be appropriately selected based on a clinically employed dose. The proportion of the compound of the present invention and the concomitant drug can be appropriately determined according to the administration subject, the administration route, the target disease, the clinical conditions, the combination, and other factors. In cases where the administration subject is a human, for instance, the concomitant drug may be used in an amount of 0.01 to 100 parts by weight per part by weight of the compound of the present invention.

Examples of the therapeutic agent for diabetes mellitus include insulin preparations (e.g., animal insulin preparations extracted from the bovine or swine pancreas; human insulin preparations synthesized by a genetic engineering technique using *Escherichia coli* or a yeast; zinc insulin; protamine zinc insulin; fragment of insulin or derivatives thereof (e.g., INS-1 etc.), and the like), agents for improving insulin resistance [e.g., pioglitazone hydrochloride, troglitazone, rosiglitazone or its maleate, GI-262570, JTT-501, MCC-555, YM-440, KRP-297, CS-011, FK-614, compounds described in WO99/58510 (e.g., (E)-4-[4-(5-methyl-2-phenyl-4-oxazolylmethoxy)benzyloxyimino]-4-phenyl-butyric acid), NN-622, AZ-242, BMS-298585, ONO-5816, LM-4156, BM-13-1258, MBX-102, GW-1536 etc.], α-glucosidase inhibitors (e.g., voglibose, acarbose, miglitol, emiglitate etc.), biguanides (e.g., phenformin, metformin, buformin etc.), insulin secretagogues [sulfonylureas (e.g., tolbutamide, glibenclamide, gliclazide, chlorpropamide, tolazamide, acetohexamide, glyclopyramide, glimepiride, glipizide, glybuzole etc.), repaglinide, nateglinide, mitiglinide or its calcium salt hydrate, GLP-1 etc.], dipeptidylpeptidase IV inhibitors (e.g., NVP-DPP-278, PT-100, NVP-DPP-728, LAF237 etc.), β3 agonists (e.g., CL-316243, SR-58611-A, UL-TG-307, SB-226552, AJ-9677, BMS-196085, AZ-40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitors, glucose-6-phosphatase inhibitors, glucagon antagonists etc.), SGLUT (sodium-glucose cotransporter) inhibitors (e.g., T-1095 etc.) and the like.

Examples of the therapeutic agent for diabetic complications include aldose reductase inhibitors (e.g., tolrestat, epalrestat, zenarestat, zopolrestat, minalrestat, fidarestat (SNK-860), CT-112 etc.), neurotrophic factors (e.g., NGF, NT-3, BDNF etc.), neurotrophic factor production-secretion promoters [e.g., neurotrophin production-secretion promoters described in WO01/14372 (e.g., 4-(4-chlorophenyl)-2-(2-methyl-1-imidazolyl)-5-[3-(2-methylphenoxy)propyl] oxazole and the like)], PKC inhibitors (e.g., LY-333531 etc.), AGE inhibitors (e.g., ALT946, pimagedine, pyratoxathine, N-phenacylthiazolium bromide (ALT766), EXO-226 etc.), reactive oxygen scavengers (e.g., thioctic acid etc.), and cerebral asodilators (e.g., tiapuride, mexiletine, etc.).

As the antihyperlipidemic agent, for example, HMG-CoA reductase inhibitors (e.g., pravastatin, simvastatin, lovastatin, atorvastatin, fluvastatin, lipantil, cerivastatin, itavastatin, ZD-4522 or salts thereof (e.g., sodium salt etc.) and the like), fibrate compounds (e.g., bezafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate and the like), squalene synthetase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), ACAT inhibitors (e.g., Avasimibe, Eflucimibe and the like), anion exchange resins (e.g., cholestyramine and the like), probucol, nicotinic acid drugs (e.g., nicomol, niceritrol and the like), ethyl eicosapentaenoate, vegetable sterol (e.g., soysterol, γ-oryzanol and the like) and the like can be mentioned.

Examples of the hypotensive agent include angiotensin converting enzyme inhibitors (e.g., captopril, enalapril, delapril, etc.), angiotensin II antagonists (e.g., candesartan cilexetil, losartan, eprosartan, valsantan, termisartan, irbesartan, tasosartan, etc.), calcium antagonists (e.g., manidipine, nifedipine, nicardipine, amlodipine, efonidipine, etc.), potassium channel openers (e.g., levcromakalim, L-27152, AL 0671, NIP-121, etc.), clonidine, and the like.

Examples of the antiobesity agent include antiobesity drugs acting on the central nervous system (e.g., dexfenfluramine, fenfluramine, phentermine, sibutramine, anfepramone, dexamphetamine, mazindol, phenylpropanolamine, clobenzorex etc.), pancreatic lipase inhibitors (e.g., orlistat etc.), β3 agonists (e.g., CL-316243, SR-58611-A, UL-TG-307, SB-226552, AJ-9677, BMS-196085, AZ-40140 etc.), anorectic peptides (e.g., leptin, CNTF (Ciliary Neurotrophic Factor) etc.), cholecystokinin agonists (e.g., lintitript, FPL-15849 etc.), and the like.

Examples of the diuretic agent include xanthine derivatives (e.g., theobromine and sodium salicylate, theobromine and calcium salicylate etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonic anhydrase inhibitors (e.g., acetazolamide etc.), chlorobenzenesulfonamide preparations (e.g., chlorthalidone, mefruside, indapamide etc.), azosemide, isosorbide, ethacrynic acid, piretanide, bumetanide, furosemide and the like.

Examples of the chemotherapeutic agent include alkylating agents (e.g., cyclophosphamide, ifosphamide etc.), metabolic antagonists (e.g., methotrexate, 5-fluorouracil and a derivative thereof etc.), antitumor antibiotics (e.g., mitomycin, adriamycin etc.), plant-derived antitumor agents (e.g., vincristine, vindesine, taxol etc.), cisplatin, carboplatin, etopoxide and the like. Of these, 5-fluorouracil derivatives such as Furtulon and Neo-Furtulon and the like are preferable.

Examples of the immunotherapeutic agent include microorganism- or bacterium-derived components (e.g., muramyl dipeptide derivatives, Picibanil etc.), immunopotentiator polysaccharides (e.g., lentinan, schizophyllan, krestin etc.), genetically engineered cytokines (e.g., interferons, interleukins (IL) etc.), colony stimulating factors (e.g., granulocyte colony stimulating factor, erythropoietin etc.) and the like. Of these, interleukins such as IL-1, IL-2, IL-12 and the like are preferable.

As the antithrombotic agent, for example, heparin (e.g., heparin sodium, heparin calcium, dalteparin sodium and the like), warfarin (e.g., warfarin potassium and the like), antithrombins (e.g., argatroban and the like), thrombolytic agent (e.g., urokinase, tisokinase, alteplase, nateplase, monteplase, pamiteplase and the like), platelet aggregation inhibitors (e.g., ticlopidine hydrochloride, cilostazol, ethyl eicosapentaenoate, beraprost sodium, sarpogrelate hydrochloride and the like) and the like can be mentioned.

As the cachexia improving agent, for example, cyclooxygenase inhibitors (e.g., indomethacin etc.) (*Cancer Research*, vol. 49, pp. 5935–5939, 1989), progesterone derivatives (e.g., megestrol acetate) (*Journal of Clinical Oncology*, vol. 12, pp. 213–225, 1994), glucosteroids (e.g., dexamethasone etc.), metoclopramide pharmaceuticals, tetrahydrocannabinol pharmaceuticals (the above references are applied to both), fat metabolism ameliorating agents (e.g., eicosapentaenoic acid etc.) (*British Journal of Cancer*, vol. 68, pp. 314–318, 1993), growth hormones, IGF-1, and antibodies to the cachexia-inducing factor TNF-α, LIF, IL-6 or oncostatin M, and the like can be mentioned.

As the concomitant drug, moreover, neuroregeneration promoters (e.g., Y-128, VX-853, prosaptide etc.), antidepressants (e.g., desipramine, amitriptyline, imipramine, etc.), antiepileptics (e.g., lamotrigine etc.), antiarrhythmic drug (e.g., mexiletine etc.), acetylcholine receptor ligands (e.g., ABT-594 etc.), endothelin receptor antagonists (e.g., ABT-627 etc.), monoamine uptake inhibitors (e.g., tramadol etc.), narcotic analgesics (e.g., morphine etc.), GABA receptor agonists (e.g., gabapentin etc.), α2 receptor agonists (e.g., clonidine etc.), local analgesics (e.g., capsaicin etc.), protein kinase C inhibitors (e.g., LY-333531 etc.), antianxiety drugs (e.g., benzodiazepine etc.), hosphodiesterase inhibitors (e.g., sildenafil (citrate) etc.), dopamine agonists (e.g., apomorphine etc.), therapeutic agents for osteoporosis (e.g., alfacalcidol, calcitriol, elcatonin, calcitonin salmon, estriol, ipriflavone, pamidronate disodium, alendronate sodium hydrate, incadronate disodium etc.), antidementia agents (e.g., tacrine, donepezil, rivastigmine, galantamine etc.), therapeutic agents for incontinentia or pollakiuria (e.g., flavoxate hydrochloride, oxybutynin hydrochloride, propiverine hydrochloride etc.), midazolam, ketoconazole and the like can be mentioned.

The concomitant drug is preferably an insulin preparation, an agent for improving insulin resistance, an α-glucosidase inhibitor, a biguanide, an insulin secretagogue (preferably a sulfonylurea) and the like.

The above concomitant drugs can be used as in a combination of two or more species in an appropriate ratio. When two or more concomitant drugs are to be used, preferable combinations include, for example, the following.

1) an agent for improving insulin resistance and an insulin preparation;
2) an agent for improving insulin resistance and an insulin secretagogue;
3) an agent for improving insulin resistance and an α-glucosidase inhibitor;
4) an agent for improving insulin resistance and a biguanide;
5) an insulin preparation and a biguanide;
6) an insulin preparation and an insulin secretagogue;
7) an insulin preparation and an α-glucosidase inhibitor;
8) an insulin secretagogue and an α-glucosidase inhibitor;
9) an insulin secretagogue and a biguanide;
10) an agent for improving insulin resistance, a insulin preparation and a biguanide;
11) an agent for improving insulin resistance, an insulin preparation and an insulin secretagogue;
12) an agent for improving insulin resistance, an insulin preparation and an α-glucosidase inhibitor;
13) an agent for improving insulin resistance, an insulin secretagogue and a biguanide;
14) an agent for improving insulin resistance, an insulin secretagogue and an α-glucosidase inhibitor; and
15) an agent for improving insulin resistance, a biguanide and an α-glucosidase inhibitor.

When the compound of the present invention is used in combination with a concomitant drug, the amount of each agent can be reduced within a safe range by taking their adverse effects into consideration. Particularly, the dose of an agent for improving insulin resistance, an insulin secretagogue and a biguanide can be reduced as compared with the normal dose. Accordingly, an adverse effect which may be caused by these agents can be safely prevented. In addition, the dose of a therapeutic agent for diabetic complications, an antihyperlipidemic agent and a hypotensive agent can be reduced, whereby an adverse effect which may be caused by these agents can be effectively prevented.

The production methods of the compound of the present invention are explained in the following.

Compound (I) [including Compounds (I-1), (I-2) and (I-3)] can be produced according to a method known per se, such as Method A to Method C shown in the following or a method analogous thereto. In each of the following production methods, the starting material may be used in the form of a salt, and as such salt, those exemplified as the aforementioned salts of Compound (I) can be used.

[Method A]

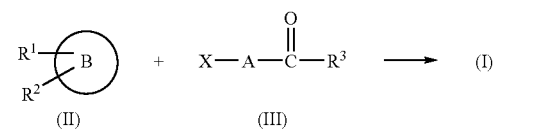

wherein X is a leaving group, and other symbols are as defined above.

As the leaving group for X, for example, a halogen atom, —OSO$_2$R$^{11}$ (R$^{11}$ is a hydrocarbon group optionally substituted by a halogen atom) and the like can be mentioned.

Here, as the halogen atom, for example, chlorine, bromine, iodine and the like can be mentioned.

As the "hydrocarbon group" of the "hydrocarbon group optionally substituted by a halogen atom" for R$^{11}$, for example, an alkyl group having 1 to 4 carbon atoms, an aryl group having 6 to 10 carbon atoms, which is optionally substituted by an alkyl group having 1 to 4 carbon atoms, an aralkyl group having 7 to 14 carbon atoms, which is optionally substituted by an alkyl group having 1 to 4 carbon atoms, and the like can be mentioned.

Here, as the alkyl group having 1 to 4 carbon atoms of the "alkyl group having 1 to 4 carbon atoms", the "aryl group having 6 to 10 carbon atoms, which is optionally substituted by an alkyl group having 1 to 4 carbon atoms" and the "aralkyl group having 7 to 14 carbon atoms, which is optionally substituted by an alkyl group having 1 to 4 carbon atoms", methyl, ethyl, propyl, isopropyl, butyl, isobutyl, sec.-butyl and t.-butyl can be mentioned, with preference given to methyl.

As the aryl group having 6 to 10 carbon atoms of the "aryl group having 6 to 10 carbon atoms, which is optionally substituted by an alkyl group having 1 to 4 carbon atoms", phenyl and naphthyl can be mentioned. Of these, phenyl is preferable.

As the aralkyl group having 7 to 14 carbon atoms of the "aralkyl group having 7 to 14 carbon atoms, which is optionally substituted by an alkyl group having 1 to 4 carbon atoms", benzyl, phenethyl and naphthylmethyl can be mentioned. Of these, benzyl is preferable.

The above-mentioned "hydrocarbon group" may have 1 to 10 halogen atoms (e.g., fluorine, chlorine, bromine, iodine and the like) at substitutable position(s).

The "hydrocarbon group optionally substituted by a halogen atom" for $R^{11}$ is preferably an alkyl group having 1 to 4 carbon atoms, which is optionally substituted by 1 to 9 halogen atoms (preferably fluorine). Of these, trifluoromethyl, pentafluoroethyl, heptafluoropropyl, nonafluorobutyl and the like are preferable.

In this method, Compound (I) is produced by the reaction of Compound (II) with Compound (III).

This reaction is carried out according to a method known per se or a method analogous thereto. For example, this reaction includes reacting Compound (II) with an organic lithium compound (e.g., n-butyl lithium, t-butyl lithium, diisobutyl lithium amide and the like), reacting the resulting compound with a metal halide (e.g., zinc chloride, magnesium bromide, tributyltin chloride and the like) or trialkoxyborane (e.g., trimethoxyborane, triisopropoxyborane and the like) and further reacting the resulting compound with Compound (III) in the presence of a transition metal catalyst (e.g., tetrakis triphenylphosphine palladium(0), tetrakis triphenylphosphine nickel(0) and the like).

This reaction is carried out in a solvent inert to the reaction.

The amount of the organic lithium compound to be used is generally 0.5 to 3 molar equivalents relative to Compound (II).

The amount of the metal halide or the trialkoxyborane to be used is generally 0.5 to 3 molar equivalents relative to Compound (II).

The amount of the transition metal catalyst to be used is generally 0.001 to 2 molar equivalents relative to Compound (II).

The amount of Compound (III) to be used is generally 0.5 to 3 molar equivalents relative to Compound (II).

As the solvent inert to the reaction, for example, aromatic hydrocarbons such as benzene, toluene, xylene and the like; aliphatic hydrocarbons such as hexane and the like; ethers such as tetrahydrofuran, dioxane, diethyl ether and the like; and the like can be mentioned. These solvents may be mixed at appropriate ratios and used.

The reaction time is generally 1 to 24 hrs.

The reaction temperature is generally −78° C. to 200° C.

Compound (I) thus obtained can be isolated or purified by known separation or purification means, such as concentration, concentration under reduced pressure, solvent extraction, crystallization, recrystallization, phase transfer, chromatography and the like.

Compound (Ib) comprised in the formula (I), wherein $R^3$ is —OH, can be also produced according to, for example, the following Method B.

[Method B]

$$R^1_{R^2}\!\!-\!\!B\!\!-\!\!A\!\!-\!\!\overset{O}{\underset{\|}{C}}\!\!-\!\!OR^{4a} \longrightarrow R^1_{R^2}\!\!-\!\!B\!\!-\!\!A\!\!-\!\!\overset{O}{\underset{\|}{C}}\!\!-\!\!OH$$

(Ia) (Ib)

wherein $R^{4a}$ is an optionally substituted hydrocarbon group and other symbols are as defined above.

In this method, Compound (Ia) is subjected to a hydrolysis reaction to give Compound (Ib).

This reaction is carried out according to a conventional method in the presence of an acid or a base in an aqueous solvent.

As the acid, for example, inorganic acids such as hydrochloric acid, sulfuric acid, hydrobromic acid and the like; organic acids such as acetic acid and the like; and the like can be mentioned.

As the base, for example, alkali metal carbonates such as potassium carbonate, sodium carbonate and the like; alkali metal alkoxides such as sodium methoxide and the like; alkali metal hydroxides such as potassium hydroxide, sodium hydroxide, lithium hydroxide and the like; and the like can be mentioned.

The amount of the acid or base to be used is generally an excess amount relative to Compound (Ia). The amount of the acid to be used is preferably about 2 to about 50 equivalents relative to Compound (Ia), and the amount of the base to be used is preferably about 1.2 to about 10 equivalents relative to Compound (Ia).

As the aqueous solvent, for example, a mixed solvent of one or more solvents selected from alcohols such as methanol, ethanol and the like; ethers such as tetrahydrofuran, dioxane, diethyl ether and the like; sulfoxides such as dimethyl sulfoxide and the like; ketones such as acetone and the like; and the like, and water at appropriate ratios, and the like can be mentioned.

The reaction temperature is generally about −20° C. to about 150° C., preferably about −10° C. to about 100° C.

The reaction time is generally about 0.1 to about 20 hrs.

Compound (Ib) thus obtained can be isolated or purified by known separation or purification means, such as concentration, concentration under reduced pressure, solvent extraction, crystallization, recrystallization, phase transfer, chromatography and the like.

Compound (Ia) used as the starting material in the above-mentioned Method B can be produced according to, for example, the above-mentioned Method A.

Compound (Ic) comprised in the formula (I), wherein $R^3$ is —$NR^5R^6$ ($R^5$ and $R^6$ are as defined above), can be also produced according to, for example, the following Method C.

[Method C]

$$(Ib) + H\!-\!NR^5R^6 \longrightarrow R^1_{R^2}\!\!-\!\!B\!\!-\!\!A\!\!-\!\!\overset{O}{\underset{\|}{C}}\!\!-\!\!NR^5R^6$$

(IV) (Ic)

wherein the symbols in the formulas are as defined above.

In this method, Compound (Ib) is subjected to an amidation reaction to give Compound (Ic).

This reaction is carried out according to a method known per se, such as i) a method comprising direct condensation of Compound (Ib) and Compound (IV), using a condensing agent, ii) a method comprising reacting a reactive derivative of Compound (Ib) with Compound (IV), and the like.

The above-mentioned i) and ii) are explained in detail in the following.

i) Method Using a Condensing Agent

In this method, Compound (Ib), Compound (IV) and a condensing agent are reacted in a solvent inert to the reaction.

The amount of Compound (IV) to be used is generally 0.1 to 10 molar equivalents, preferably 0.3 to 3 molar equivalents, relative to Compound (Ib).

As the condensing agent, for example, dicyclohexylcarbodiimide (DCC), 1-ethyl-3-(3-dimethylaminopropyl)carbodiimide hydrochloride (WSC) and the like can be mentioned. Of these, DCC is preferable.

The amount of the condensing agent to be used is generally 0.1 to 10 molar equivalents, preferably 0.3 to 3 molar equivalents, relative to Compound (Ib).

As the solvent inert to the reaction, for example, nitrites such as acetonitrile and the like; amides such as N,N-dimethylformamide and the like; halogenated hydrocarbons such as dichloromethane, chloroform and the like; ethers such as tetrahydrofuran, dioxane, diethyl ether and the like; and the like can be mentioned. These solvents may be mixed at appropriate ratios and used.

The reaction temperature is generally −30° C. to 100° C.

The reaction time is generally 0.5 to 20 hrs.

This reaction may be carried out in the presence of 1 to 1.5 equivalents of 1-hydroxybenzotriazole (HOBT) or a catalytic amount to 5 equivalents of a base, as necessary.

As the base, for example,
1) a strong base such as alkali metal or alkali earth metal hydride (e.g., lithium hydride, sodium hydride, potassium hydride, calcium hydride and the like), alkali metal or alkali earth metal amide (e.g., lithium amide, sodium amide, lithium diisopropylamide, lithium dicyclohexylamide, lithium hexamethyldisilazide, sodium hexamethyldisilazide, potassium hexamethyldisilazide and the like), alkali metal or alkali earth metal lower alkoxide (e.g., sodium methoxide, sodium ethoxide, potassium tert-butoxide and the like) and the like;
2) an inorganic base such as alkali metal or alkali earth metal hydroxide (e.g., sodium hydroxide, potassium hydroxide, lithium hydroxide, barium hydroxide and the like), alkali metal or alkali earth metal carbonate (e.g., sodium carbonate, potassium carbonate, cesium carbonate and the like), alkali metal or alkali earth metal hydrogen carbonate (e.g., sodium hydrogen carbonate, potassium hydrogen carbonate and the like) and the like;
3) an organic base such as amines (e.g., triethylamine, diisopropylethylamine, N-methylmorpholine, N,N-dimethylaminopyridine, N,N-dimethylaniline, DBU (1,8-diazabicyclo[5.4.0]undec-7-ene), DBN (1,5-diazabicyclo[4.3.0]non-5-ene) and the like); a basic heterocyclic compound such as pyridine, imidazole, 2,6-lutidine and the like; and the like, and the like can be mentioned.

Of the above-mentioned bases, triethylamine, 4-dimethylaminopyridine and the like are preferable.

ii) Method Using a Reactive Derivative of Compound (Ib)

In this method, a reactive derivative of Compound (Ib) is reacted with Compound (IV) in a solvent inert to the reaction.

As the "reactive derivative of Compound (Ib)", for example, acid halides (e.g., acid chlorides, acid bromides and the like), mixed acid anhydrides (e.g., acid anhydrides with $C_{1-6}$ alkyl-carboxylic acids, $C_{6-10}$ aryl-carboxylic acids or $C_{1-6}$ alkyl carbonic acids (e.g., methyl carbonic acid, ethyl carbonic acid, isobutyl carbonic acid and the like), and the like), active esters (e.g., ester with phenol optionally having substituents, 1-hydroxybenzotriazole or N-hydroxy succinimide, and the like), imidazolide and the like can be mentioned.

As the "substituent" of the "phenol optionally having substituents", for example, halogen atoms (e.g., fluorine, chlorine, bromine, iodine and the like), nitro, optionally halogenated $C_{1-6}$ alkyl and optionally halogenated $C_{1-6}$ alkoxy can be mentioned. The number of substituents is, for example, 1 to 5.

Specific examples of the "phenol optionally having substituents" include phenol, pentachlorophenol, pentafluorophenol, p-nitrophenol and the like. The reactive derivative is preferably an acid halide.

As the solvent inert to the reaction, for example, aromatic hydrocarbons such as benzene, toluene, xylene and the like; nitrites such as acetonitrile and the like; amides such as N,N-dimethylformamide and the like; halogenated hydrocarbons such as dichloromethane, chloroform and the like; ethers such as tetrahydrofuran, dioxane, diethyl ether and the like; sulfoxides such as dimethyl sulfoxide and the like; ketones such as acetone and the like; water and the like can be mentioned. These solvents may be mixed at appropriate ratios and used.

The amount of Compound (IV) to be used is generally 0.1 to 10 molar equivalents, preferably 0.3 to 3 molar equivalents, relative to the reactive derivative of Compound (Ib).

The reaction temperature is generally −30° C. to 100° C.

The reaction time is generally 0.5 to 20 hrs.

This reaction may be carried out in the presence of a base as necessary.

As the base, those similar to the aforementioned ones are used.

The amount of the base to be used is, for example, 0.1 to 10 molar equivalents, preferably 0.3 to 3 molar equivalents, relative to the reactive derivative of Compound (Ib).

A method using an acid halide or a mixed acid anhydride as the "reactive derivative" of Compound (Ib) is specifically described in the following. ii-1)

As a method using an acid halide, a method comprising reacting Compound (Ib) with an acid halide in the presence of a base in a solvent inert to the reaction, and then reacting the resulting compound with Compound (IV) is preferable.

As the base, amines such as triethylamine, N-methylmorpholine, N,N-dimethylaniline and the like; alkali metal carbonates such as sodium carbonate, potassium carbonate and the like; alkali metal hydrogen carbonates such as sodium hydrogen carbonate and the like; and the like are preferable.

As the solvent inert to the reaction, aromatic hydrocarbons such as benzene, toluene, xylene and the like; ethers such as tetrahydrofuran, dioxane, diethyl ether and the like; amides such as N,N-dimethylformamide and the like, esters such as ethyl acetate and the like, water and the like are preferable. These solvents may be mixed at appropriate ratios and used. ii-2)

As a method using a mixed acid anhydride, a method comprising reacting Compound (Ib) with a chlorocarbonate (e.g., methyl chlorocarbonate, ethyl chlorocarbonate, isobutyl chlorocarbonate and the like) in the presence of a base, and then reacting the resulting compound with Compound (IV) is preferable.

As the base, amines such as triethylamine, N-methylmorpholine, N,N-dimethylaniline and the like, and the like are preferable.

Compound (Ic) thus obtained can be isolated or purified by known separation or purification means, such as concentration, concentration under reduced pressure, solvent extraction, crystallization, recrystallization, phase transfer, chromatography and the like.

Compound (Ib) used as the starting material in the above-mentioned Method C can be produced according to, for example, the above-mentioned Method A or Method B. In addition, Compound (IV) can be produced according to a method known per se.

Compound (II) used as the starting material in the above-mentioned Method A can be produced according to, for example, the following Method D.

[Method D]

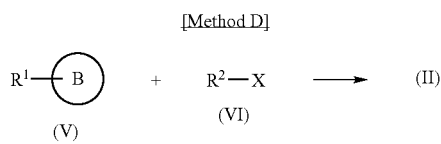

wherein the symbols in the formulas are as defined above.

In this method, Compound (V) is reacted with Compound (VI) to give Compound (II).

This reaction is carried out in the same manner as in the reaction of Compound (II) with Compound (III) in the aforementioned Method A.

Compound (V) and Compound (VI) used as the starting materials can be produced according to a method known per se.

In the above respective reactions, when the starting material has an amino group, a carboxyl group, a hydroxy group or a carbonyl group as a substituent, a protecting group generally used in the peptide chemistry and the like may be applied to the group. After the reaction, the desired compound can be obtained by removing the protecting group where necessary.

As the protecting group for the amino group, for example, formyl, $C_{1-6}$ alkyl-carbonyl (e.g., acetyl, propionyl and the like), $C_{1-6}$ alkoxy-carbonyl (e.g., methoxycarbonyl, ethoxycarbonyl, tert-butoxycarbonyl and the like), benzoyl, $C_{7-10}$ aralkyl-carbonyl (e.g., benzylcarbonyl and the like), $C_{7-14}$ aralkyloxy-carbonyl (e.g., benzyloxycarbonyl, 9-fluorenylmethoxycarbonyl and the like), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atoms (e.g., fluorine, chlorine, bromine, iodine and the like), $C_{1-6}$ alkoxy (e.g., methoxy, ethoxy, propoxy and the like), nitro and the like.

As the protecting group for the carboxyl group, for example, $C_{1-6}$ alkyl (e.g., methyl, ethyl, propyl, isopropyl, butyl, tert-butyl and the like), $C_{7-11}$ aralkyl (e.g., benzyl and the like), phenyl, trityl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atoms (e.g., fluorine, chlorine, bromine, iodine and the like), $C_{1-6}$ alkoxy (e.g., methoxy, ethoxy, propoxy and the like), nitro and the like.

As the protecting group for the hydroxy group, for example, $C_{1-6}$ alkyl (e.g., methyl, ethyl, propyl, isopropyl, butyl, tert-butyl and the like), phenyl, trityl, $C_{7-10}$ aralkyl (e.g., benzyl and the like), formyl, $C_{1-6}$ alkyl-carbonyl (e.g., acetyl, propionyl and the like), benzoyl, $C_{7-10}$ aralkyl-carbonyl (e.g., benzylcarbonyl and the like), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl and the like), $C_{2-6}$ alkenyl (e.g., 1-allyl and the like) and the like can be mentioned. These groups are optionally substituted by 1 to 3 halogen atoms (e.g., fluorine, chlorine, bromine, iodine and the like), $C_{1-6}$ alkyl (e.g., methyl, ethyl, propyl and the like), $C_{1-6}$ alkoxy (e.g., methoxy, ethoxy, propoxy and the like), nitro and the like.

Examples of the protecting group for the carbonyl group include cyclic acetals (e.g., 1,3-dioxane etc.), acyclic acetals (e.g., di-$C_{1-6}$ alkylacetals etc.) and the like.

In addition, these protecting groups can be removed according to a method known per se, such as the methods described in *Protective Groups in Organic Synthesis*, published by John Wiley and Sons (1980), and the like. For example, methods employing an acid, a base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide etc.) or the like, the reduction method, and the like may be used.

When Compound (I) contains an optical isomer, a stereoisomer, a position isomer or a rotational isomer, these isomers are also encompassed as Compound (I) and can be each obtained as a single substance by means of a method known per se of synthesis or separation. For example, when an optical isomer is present in Compound (I), the optical isomers separated from said compound are also included in Compound (I).

Optical isomers can be produced according to a method known per se. Specifically, optical isomers are obtained by using an optically active intermediate, or optically resolving a racemate of the final product according to a conventional method.

Examples of the method for optical resolution include methods known per se, such as the fractional recrystallization methods, the chiral column methods, the diastereomer methods, and the like.

1) Fractional Recrystallization Method

A method wherein salts are formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.], which salts are separated by fractional recrystallization, and, if desired, subjected to a neutralization process, to yield free optical isomers.

2) Chiral Column Method

A separation method wherein a racemate or a salt thereof is applied to a column for optical isomer separation (chiral column). In the case of liquid chromatography, for example, optical isomers are separated by adding a mixture of the optical isomers to a chiral column such as ENANTIO-OVM (produced by Tosoh Corporation) or CHIRAL series produced by DAICEL CHEMICAL IND., and developing it in water, various buffers (e.g., phosphate buffer), an organic solvent (e.g., ethanol, methanol, isopropanol, acetonitrile, trifluoroacetic acid, diethylamine etc.) alone, or a mixed solution thereof. In the case of gas chromatography, for example, a chiral column such as CP-Chirasil-DeX CB (produced by GL Science) is used to separate optical isomers.

3) Diastereomer Method

A method wherein a mixture of a racemate and an optically active reagent are chemically reacted to yield a diastereomer mixture, which is then subjected to ordinary means of separation (e.g., fractional recrystallization, chromatography etc.) and the like to obtain single substances, which are subjected to a chemical treatment such as a hydrolysis reaction to leave the optically active reagent moiety, whereby the desired optical isomer is obtained. For example, when Compound (I) has hydroxy, or primary or secondary amino in the molecule, said compound, and an optically active organic acid (e.g., MTPA [α-methoxy-α-(trifluoromethyl)phenylacetic acid], (−)-menthoxyacetic acid, etc.) and the like may be subjected to a condensing reaction to yield diastereomers of esters or amides, respectively. On the other hand, when Compound (I) has a carboxyl group, said compound and an optically active amine or alcohol reagent may be subjected to a condensing reaction to yield diastereomers of amides or esters, respectively. The diastereomers are separated and converted to optical isomers of the original compound by subjecting them to an acid hydrolysis or a basic hydrolysis reaction.

The present invention further relates to
1) an agent for the prophylaxis or treatment of diabetes mellitus, which comprises a peroxisome proliferator-activated receptor transcriptional activity promoter which is non-binding to peroxisome proliferator-activated receptors;
2) an agent for the prophylaxis or treatment of hyperlipidemia, which comprises a peroxisome proliferator-activated receptor transcriptional activity promoter which is non-binding to peroxisome proliferator-activated receptors;
3) an agent for ameliorating lipid metabolism, which comprises a peroxisome proliferator-activated receptor transcriptional activity promoter which is non-binding to peroxisome proliferator-activated receptors;
4) an agent for the prophylaxis or treatment of obesity, which contains a peroxisome proliferator-activated receptor transcriptional activity promoter which is non-binding to peroxisome proliferator-activated receptors;
5) an insulin sensitizer comprising a peroxisome proliferator-activated receptor transcriptional activity promoter which is non-binding to peroxisome proliferator-activated receptors;
6) an agent for improving insulin resistance comprising a peroxisome proliferator-activated receptor transcriptional activity promoter which is non-binding to peroxisome proliferator-activated receptors; and
7) an agent for the prophylaxis or treatment of impaired glucose tolerance, which comprises a peroxisome proliferator-activated receptor transcriptional activity promoter which is non-binding to peroxisome proliferator-activated receptors.

As used herein, "a peroxisome proliferator-activated receptor transcriptional activity promoter which is non-binding binding to peroxisome proliferator-activated receptors" is not particularly limited as long as it is a substance that promotes transcriptional activity of a peroxisome proliferator-activated receptor without binding with the peroxisome proliferator-activated receptor. As such substance, for example, the aforementioned compound of the present invention and the like can be mentioned. In addition, it is preferable that a "peroxisome proliferator-activated receptor transcriptional activity promoter which is non-binding to peroxisome proliferator-activated receptors" should not be a 1,3-azole derivative represented by the formula:

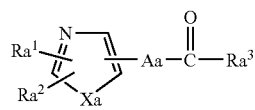

wherein
$Ra^1$ is an optionally substituted aromatic hydrocarbon group or an optionally substituted aromatic heterocyclic group;
$Ra^2$ is a hydrogen atom or an optionally substituted hydrocarbon group;
Xa is O, S or a group of the formula: —$NRa^4$— ($Ra^4$ is a hydrogen atom or an optionally substituted alkyl group);
Aa is an optionally substituted aromatic hydrocarbon group or an optionally substituted aromatic heterocyclic group; and
$Ra^3$ is a group of the formula: —$ORa^5$ ($Ra^5$ is a hydrogen atom or an optionally substituted hydrocarbon group) or —$NRa^6Ra^7$ ($Ra^6$ and $Ra^7$ are the same or different and each is a hydrogen atom or an optionally substituted hydrocarbon group, or $Ra^6$ and $Ra^7$ may form a ring together with the adjacent nitrogen atom).

The agent for the prophylaxis or treatment of diabetes mellitus, the agent for the prophylaxis or treatment of hyperlipidemia, the agent for ameliorating lipid metabolism, the agent for the prophylaxis or treatment of obesity, the insulin sensitizer, the agent for improving insulin resistance and the agent for the prophylaxis or treatment of impaired glucose tolerance according to the present invention (hereinafter sometimes to be abbreviated as the agent of the present invention) can be produced in the same manner as the aforementioned pharmaceutical compositions using "a peroxisome proliferator-activated receptor transcriptional activity promoter which is non-binding to peroxisome proliferator-activated receptors".

The agent of the present invention shows low toxicity and can be used safely in mammals (e.g., human, mouse, rat, rabbit, dog, cat, bovine, horse, swine, monkey etc.). The dose of the agent of the present invention is the same as for the aforementioned compound of the present invention. In addition, the agent of the present invention can be used in combination with the aforementioned concomitant drug in the same manner as in the compound of the present invention.

The present invention is hereinafter described in more detail by means of, but is not limited to, the following Test Examples, Reference Examples, Examples and Formulation Examples.

In the Reference Examples and Examples below, % means percent by weight, unless specified otherwise. Room temperature means the temperature of 1 to 30° C.

Abbreviations for bases, amino acids and others used in the present specification are based on abbreviations specified by the IUPAC-IUB Commission on Biochemical Nomenclature or abbreviations in common use in the art.

The SEQ ID NOs of the sequence listing in the present specification show the following sequences.

[SEQ ID NO: 1]
A base sequence of primer PAG-U used in Reference Example 1.

[SEQ ID NO: 2]
A base sequence of primer PAG-L used in Reference Example 1.

[SEQ ID NO: 3]
A base sequence of primer XRA-U used in Reference Example 2.

[SEQ ID NO: 4]
A base sequence of primer XRA-L used in Reference Example 2.

[SEQ ID NO: 5]

A base sequence of PPRE-U used in Reference Example 4.

[SEQ ID NO: 6]

A base sequence of PPRE-L used in Reference Example 4.

[SEQ ID NO: 7]

A base sequence of primer TK-U used in Reference Example 4.

[SEQ ID NO: 8]

A base sequence of primer TK-L used in Reference Example 4.

EXAMPLES

Test Example 1

Glucose-Lowering and Lipid-Lowering (Triglyceride-Lowering) Actions in Mice

Test compounds were mixed in a powdery diet (CE-2, Japan Clea) at the proportion of 0.01%, and freely given to KKA$^y$ mice (9 to 12 weeks old, 5 mice per group), a model of obesity-non-insulin dependent diabetes mellitus (type 2 diabetes mellitus), for four days. During this period, water was given freely. Blood was sampled from orbital venous plexus, and glucose and triglyceride levels in plasma separated from the blood were determined enzymatically using L type Wako Glu2 (Wako Pure Chemical Industries, Ltd.) or L type Wako TG-H (Wako Pure Chemical Industries, Ltd.), respectively. The results are given in [Table 1].

In the Table, "glucose-lowering action (%)" represents a reduction percent (%) of the blood glucose level in a test compound administration group when the blood glucose level in a test compound non-administration group is taken as 100%. In addition, "lipid-lowering action (%)" represents a reduction percent (%) of the blood triglyceride level in the test compound administration group when the blood triglyceride level in the test compound non-administration group is taken as 100%.

TABLE 1

| test compound (Example number) | glucose-lowering action (%) | lipid-lowering action (%) |
| --- | --- | --- |
| 10 | 37 | 62 |
| 15 | 30 | 54 |
| 58 | 37 | 48 |

As shown above, it is clear that the compounds of the present invention have a superior glucose-lowering action and a lipid-lowering action, and is useful as an agent for the prophylaxis or treatment of diabetes mellitus, hyperlipidemia (particularly, hypertriglyceridemia), impaired glucose tolerance or the like.

Test Example 2

(PPARγ-RXRα Heterodimer Ligand Activity)

PPARγ: RXRα: 4ERPP/CHO-K1 cells obtained in the following Reference Example 5 were cultured in HAM F12 medium (manufactured by NISSUI SEIYAKU) containing 10% fetal bovine serum [manufactured by Life Technologies, Inc., USA], seeded in a 96-well white plate [manufactured by Corning Coster Corporation, USA] at the density of $2 \times 10^4$ cells/well and cultured in a $CO_2$ gas incubator at 37° C. overnight.

After washing the 96-well white plate with PBS (Phosphate-buffered saline), 90 µl of HAM F12 medium containing 0.1% fatty acid-free bovine serum albumin (BSA) and 10 µl of test compound were added, and the cells were cultured in a $CO_2$ gas incubator at 37° C. for 48 hrs. The medium was removed and 40 µl of PicaGene 7.5 (manufactured by Wako Pure Chemical Industries, Ltd.) was added. After stirring, the luciferase activity was determined using Lumistar [manufactured by BMG Labtechnologies GmbH, Germany].

The fold induction was calculated from the luciferase activity of each test compound when the luciferase activity of the test compound non-administration group is taken as 1. The values of the test compound concentration and the fold induction were analyzed using PRISM 2.01 (produced by GraphPad Software Inc. USA) to calculate the $EC_{50}$ values, the concentration of a test compound for 50% of the maximum fold induction. The results are shown in [Table 2].

TABLE 2

| test compound (Example number) | $EC_{50}$ (nM) |
| --- | --- |
| 7 | 7.6 |
| 9 | 54 |
| 6 | 3.6 |
| 10 | 3.8 |
| 15 | 22 |
| 16 | 23 |
| 26 | 23 |
| 27 | 2.1 |
| 28 | 2.3 |
| 29 | 0.59 |
| 30 | 6.0 |
| 33 | 2.7 |
| 34 | 1.2 |
| 35 | 3.8 |
| 44 | 68 |

These results indicate that the compounds of the present invention have a superior PARγ-RXRα heterodimer ligand activity.

Reference Example 1

Cloning of Human PPARγ Gene

Human PPARγ gene was cloned by a PCR method using heart cDNA (produced by Toyobo Co., Ltd., trade name: QUICK-Clone cDNA) as a template, and a primer set shown below which was prepared by reference to the base sequence of PPARγ gene reported by Greene et al. [*Gene Expr.*, 1995, vol. 4(4–5), pp. 281–299].

PAG-U: 5'-GTG GGT ACC GAA ATG ACC ATG GTT GAC ACA GAG-3' (SEQ ID NO: 1)

PAG-L: 5'-GGG GTC GAC CAG GAC TCT CTG CTA GTA CAA GTC-3' (SEQ ID NO: 2)

The PCR reaction was performed by Hot Start method using AmpliWax PCR Gem 100 (produced by TAKARA SHUZO CO., LTD.). First, 2 µl of 10×LA PCR Buffer, 3 µl of 2.5 mM dNTP solution, 2.5 µl each of 12.5 µM primer solutions and 10 µl of sterilized distilled water were mixed to obtain a bottom layer solution mixture. One µl of human heart cDNA (1 ng/ml) as a template, 3 µl of 10×LA PCR Buffer, 1 µl of 2.5 mM DNTP solution, 0.5 µl of TaKaRa LA Taq DNA polymerase (produced by TAKARA SHUZO CO., LTD.) and 24.5 µl of sterilized distilled water were mixed to obtain a top layer solution mixture.

To the bottom layer solution mixture described above was added one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture for PCR. A tube containing the reaction mixture was set on a thermal cycler (produced by Perkin Elmer, USA) and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector (produced by TAKARA SHUZO CO., LTD.) to obtain plasmid pTBT-hPPARγ.

Reference Example 2

Cloning of Human RXRα Gene

A human RXRα gene was cloned by a PCR method using kidney cDNA (produced by Toyobo Co., Ltd., trade name: QUICK-Clone cDNA) as a template, and a primer set shown below which was prepared with reference to the base sequence of RXRα gene reported by Mangelsdorf, D. J. et al. (*Nature*, 1990, Vol. 345 (6272), page 224–229).

XRA-U: 5'-TTA GAA TTC GAC ATG GAC ACC AAA CAT TTC CTG-3' (SEQ ID NO: 3)
XRA-L: 5'-CCC CTC GAG CTA AGT CAT TTG GTG CGG CGC CTC-3' (SEQ ID NO: 4)

The PCR reaction was performed by Hot Start method using AmpliWax PCR Gem 100 (produced by TAKARA SHUZO CO., LTD.). First, 2 µl of 10×LA PCR Buffer, 3 µl of 2.5 mM DNTP solution, 2.5 µl each of 12.5 µM primer solutions and 10 µl of sterilized distilled water were mixed to obtain a bottom layer solution mixture. One µl of human kidney cDNA (1 ng/ml) as a template, 3 µl of 10×LA PCR Buffer, 1 µl of 2.5 mM dNTP solution, 0.5 µl of TaKaRa LA Taq DNA polymerase (produced by TAKARA SHUZO CO., LTD.) and 24.5 µl of sterilized distilled water were mixed to obtain a top layer solution mixture.

To the bottom layer solution mixture described above was added one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture for PCR. A tube containing the reaction mixture was set on a thermal cycler (produced by Perkin Elmer, USA) and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector (produced by TAKARA SHUZO CO., LTD.) to obtain plasmid pTBT-hRXRα.

Reference Example 3

Construction of Expression Plasmids for Human PPARγ and RXRα

A 7.8 kb FspI-NotI fragment of plasmid pVgRXR (produced by Invitrogen, USA) was ligated to a 0.9 kb FspI-NotI fragment containing RXRα gene of plasmid pTBT-hRXRα obtained in Reference Example 2 to prepare plasmid pVgRXR2. Then, pVgRXR2 was digested with BstXI, and then treated with T4DNA polymerase (produced by TAKARA SHUZO CO., LTD.) to give a blunt-ended product. Then digestion with KpnI gave a 6.5 kb DNA fragment.

On the other hand, plasmid pTBT-hPPARγ obtained in Reference Example 1 was digested with Sal I, and then treated with T4DNA polymerase (produced by TAKARA SHUZO CO., LTD.) to give a blunt-ended product. Then digestion with KpnI gave a 1.4 kb DNA fragment containing human PPARγ gene.

The both DNA fragments were ligated to construct plasmid pVgRXR2-hPPARγ.

Reference Example 4

Construction of Reporter Plasmids

A DNA fragment containing PPAR-response element (PPRE) of an acyl CoA oxidase was prepared using the following 5'-terminal phosphorylated synthetic DNA.

```
PPRE-U:  5'-pTCGACAGGGGACCAGGACAAAGGTCACGTTCGGGAG-3'   (SEQ ID NO: 5)

PPRE-L:  5'-pTCGACTCCCGAACGTGACCTTTGTCCTGGTCCCCTG-3'   (SEQ ID NO: 6)
```

First, PPRE-U and PPRE-L were annealed and inserted to Sal I site of plasmid pBlueScript SK+. By determining the base sequence of the inserted fragment, plasmid pBSS-PPRE4, in which 4 PPREs were ligated in tandem, was selected.

An HSV thymidine kinase minimum promoter (TK promoter) region was cloned by a PCR method using pRL-TK vector (produced by Promega, USA) as a template, and a primer set shown below which was prepared with reference to the base sequence of the promoter region of thymidine kinase gene reported by Luckow, B et al. (*Nucleic Acids Res.*, 1987, Vol. 15(13), p. 5490)

```
TK-U:   5'-CCCAGATCTCCCCAGCGTCTTGTCATTG-3'   (SEQ ID NO: 7)

TK-L:   5'-TCACCATGGTCAAGCTTTTAAGCGGGTC-3'   (SEQ ID NO: 8)
```

The PCR reaction was performed by Hot Start method using AmpliWax PCR Gem 100 (TAKARA SHUZO CO., LTD.). First, 2 µl of 10×LA PCR Buffer, 3 µl of 2.5 mM dNTP solution, 2.5 µl each of 12.5 µM primer solutions and 10 µl of sterilized distilled water were mixed to obtain a bottom layer solution mixture. One µl of pRL-TK vector (produced by Promega, USA) as a template, 3 µl of 10×LA PCR Buffer, 1 µl of 2.5 mM dNTP solution, 0.5 µl of TaKaRa LA Taq DNA polymerase (produced by TAKARA SHUZO CO., LTD.) and 24.5 µl of sterilized distilled water were mixed to obtain a top layer solution mixture.

To the bottom layer solution mixture described above was added one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture for PCR. A tube containing the reaction mixture was set on a thermal cycler (produced by Perkin Elmer, USA) and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 140 b DNA fragment containing TK promoter was recovered from the gel, and then inserted into pT7 Blue-T vector (produced by TAKARA SHUZO CO., LTD.). By digesting the plasmid thus obtained with the restriction enzymes Bg1 II and NcoI, a fragment containing TK promoter was obtained, which was ligated to the Bg1 II-NcoI fragment of plasmid pGL3-Basic vector (produced by Promega, USA) to obtain plasmid pGL3-TK.

A 4.9 kb NheI-XhoI fragment of plasmid pGL3-TK thus obtained was ligated to a 200 b NheI-XhoI fragment of plasmid pBSS-PPRE4 to obtain plasmid pGL3-4ERPP-TK.

This plasmid pGL3-4ERPP-TK was digested with BamHI (produced by TAKARA SHUZO CO., LTD.), and then treated with T4DNA polymerase (produced by TAKARA SHUZO CO., LTD.) to form a blunt-end, whereby obtaining a DNA fragment.

On the other hand, pGFP-C1 (produced by Toyobo Co., Ltd.) was digested with Bsu36I (NEB), and then treated with T4DNA polymerase (produced by TAKARA SHUZO CO., LTD.) to form a blunt-end whereby obtaining a 1.6 kb DNA fragment.

The both DNA fragments were ligated to construct a reporter plasmid pGL3-4ERPP-TK neo.

Reference Example 5

Introduction of Human PPARγ- and RXRα-Expression Plasmid and Reporter Plasmid into CHO-K1 Cell as Well as Establishment of Expressed Cell A CHO-K1 cell cultured in a tissue culture flask (750 ml) [produced by Corning Costar Corporation, USA] containing HAM F12 medium (produced by NISSUI SEIYAKU) supplemented with 10% fetal bovine serum [produced by Life Technologies, Inc., USA] was scraped by treating with 0.5 g/L trypsin-0.2 g/L EDTA (ethylenediamine tetraacetate) [produced by Life Technologies, Inc., USA], and then the cell was washed with PBS (Phosphate-buffered saline)[produced by Life Technologies, Inc., USA], centrifuged (1000 rpm, 5 minutes) and suspended in PBS. Subsequently, DNA was introduced into the cell under the conditions shown below using GENE PULSER (produced by Bio-Rad Laboratories, USA).

Namely, to a cuvette having a 0.4 cm gap were added $8 \times 10^6$ cells and 10 µg of plasmid pVgRXR2-hPPARγ obtained in Reference Example 3 and 10 µg of reporter plasmid pGL3-4ERPP-TK neo obtained in Reference Example 4, which was subjected to electroporation at the voltage of 0.25 kV under the capacitance of 960 µF. Subsequently, the cell was transferred into a HAM F12 medium containing 10% fetal bovine serum and cultured for 24 hours, and then the cell was scraped again and centrifuged, and then suspended in HAM F12 medium containing 10% fetal bovine serum supplemented with 500 µg/ml of Geneticin [produced by Life Technologies, Inc., USA] and 250 µg/ml of Zeocin (produced by Invitrogen, USA). The obtained suspension was diluted to the density of $10^4$ cells/ml and inoculated in a 96-well plate [produced by Corning Costar Corporation, USA], which was cultured in a $CO_2$ gas incubator at 37° C., whereby obtaining a Geneticin- and Zeocin-resistant transformant.

Subsequently, after the transformant cell line thus obtained was cultured in a 24-well plate [produced by Corning Costar Corporation, USA], a cell line in which the luciferase was expressed and induced, i.e., PPARγ: RXRα: 4ERPP/CHO-K1 cell was selected by the addition of 10 µM pioglitazone hydrochloride.

Reference Example 6

To a solution (50 ml) of 1-methylpyrrole (4.44 ml) in tetrahydrofuran was added dropwise t-butyl lithium (1.7 M solution in pentane, 30.0 ml) under an argon atmosphere at −78° C. This mixed solution was heated to room temperature, and a solution (100 ml) of zinc chloride (75.0 g) in tetrahydrofuran was added. This mixture was stirred for 1 hr., and 1-bromo-4-trifluoromethylbenzene (3.50 ml) and tetrakis(triphenylphosphine)palladium (0.722 g) were added. This mixture was stirred overnight under an argon atmosphere, and poured into 0.5 M hydrochloric acid. The mixture was extracted with ethyl acetate. The organic layer was washed with saturated aqueous sodium hydrogen carbonate solution and saturated brine, dried over anhydrous magnesium sulfate and concentrated. The residue was purified by silica gel column chromatography (hexane:ethyl acetate=5:1, volume ratio) to give 1-methyl-2-(4-trifluoromethylphenyl)pyrrole (4.01 g, yield 71%) as a colorless crystalline powder. melting point: 39–40° C.

Reference Example 7

A mixture of 5-iodosalicylic acid (6.60 g), benzyl bromide (6.54 ml), potassium carbonate (13.8 g) and N,N-dimethylformamide (100 ml) was stirred at room temperature for 2 hrs. and poured into water. The mixture was extracted with ethyl acetate. The organic layer was washed three times with water and once with saturated brine, dried over anhydrous magnesium sulfate and concentrated. The residue was purified by silica gel column chromatography (hexane:ethyl acetate=10:1, volume ratio), and crystallized from hexane-ethyl acetate to give benzyl 2-benzyloxy-5-iodobenzoate (7.75 g, yield 70%) as colorless plate crystals. melting point: 72–73° C.

Reference Example 8

A mixture of 3-cyanobenzaldehyde (9.81 g), ethylene glycol (9.31 g), p-toluenesulfonic acid monohydrate (0.07 g) and toluene (200 ml) was heated under reflux for 15 hrs., while removing generated water with a Dean-Stark trap. After cooling, the reaction mixture was concentrated, and the residue was diluted with ethyl acetate. This solution was washed with saturated aqueous sodium hydrogen carbonate solution and saturated brine, dried over anhydrous magnesium sulfate, and concentrated to give 3-(1,3-dioxolan-2-yl) benzonitrile (13.1 g, yield 100%) as a colorless oil. NMR (CDCl₃) δ: 4.01–4.17 (4H, m), 5.83 (1H, s), 4.50 (1H, t, J=7.6 Hz), 7.63–7.74 (2H, m), 7.80 (1H, t, J=1.6 Hz).

Reference Example 9

A mixture of 4-(1,3-dioxolan-2-yl)benzonitrile (1.0 g), sodium azide (1.48 g), triethylamine hydrochloride (1.18 g) and 1-methyl-2-pyrrolidinone (50 ml) was stirred at 150° C. for 3 hrs. After cooling, 1 M hydrochloric acid and water were added to the reaction mixture to adjust to pH=3 to 4. The mixture was extracted with ethyl acetate. The organic layer was washed with water and saturated brine, dried over anhydrous magnesium sulfate and concentrated. The residue was recrystallized from ethyl acetate to give 5-[4-(1,3-dioxolan-2-yl)phenyl]-1H-tetrazole (0.300 g, yield 24%) as brown prism crystals. melting point: 197–199° C. (decomposition).

Reference Example 10

A mixture of 3-(1,3-dioxolan-2-yl)benzonitrile (7.0 g), sodium azide (10.4 g), triethylamine hydrochloride (8.26 g) and 1-methyl-2-pyrrolidinone (200 ml) was stirred at 150° C. for 4 hrs. After cooling, 1 M hydrochloric acid and water were added to the reaction mixture to adjust to pH=3 to 4. The mixture was extracted with ethyl acetate. The organic layer was washed with water and saturated brine, dried over anhydrous magnesium sulfate and concentrated. A mixture of the residue, 4-(trifluoromethyl)benzoyl chloride (3.27 ml) and pyridine (100 ml) was heated under reflux for 1 hr. After cooling, water was added to the reaction mixture, and the mixture was extracted with ethyl acetate. The organic layer was washed with 1 M hydrochloric acid, water and saturated brine, dried over anhydrous magnesium sulfate and concentrated. The residue was purified by silica gel column chromatography (hexane:ethyl acetate=3:1, volume ratio) to give 2-[3-(1,3-dioxolan-2-yl)phenyl]-5-(4-trifluoromethylphenyl)-1,3,4-oxadiazole (4.30 g, yield 54%). Recrystallization from hexane-ethyl acetate gave colorless prism crystals. melting point: 107–108° C.

Reference Example 11

A mixture of 2-nitrobenzoyl chloride (0.190 g), 5-[4-(1,3-dioxolan-2-yl)phenyl]-1H-tetrazole (0.200 g) and pyridine (5 ml) was heated under reflux for 1 hr. After cooling, water was added to the reaction mixture, and the crystals were collected by filtration, and dissolved in ethyl acetate. This solution was washed with 1 M hydrochloric acid, water and saturated brine, dried over anhydrous magnesium sulfate and concentrated. The residue was washed with hexane to give 2-[4-(1,3-dioxolan-2-yl)phenyl]-5-(2-nitrophenyl)-1,3,4-oxadiazole (0.240 g, yield 77%). Recrystallization from hexane-ethyl acetate gave colorless prism crystals. melting point: 88–89° C.

Reference Example 12

To a solution (50 ml) of 4-trifluoromethylbenzohydrazide (3.06 g) and benzaldehyde (1.52 ml) in methanol was added dropwise conc. sulfuric acid (0.5 ml), and this mixture was stirred at room temperature for 1 hr. The reaction mixture was concentrated, and the residue was washed with hexane-ethanol (1:1, volume ratio) and recrystallized from ethanol to give N'-benzylidene-4-trifluoromethylbenzohydrazide (3.23 g, yield 74%) as colorless needle crystals. melting point: 216–217° C.

Reference Example 13

A mixture of N'-benzylidene-4-trifluoromethylbenzohydrazide (2.92 g), thionyl chloride (1.09 ml) and toluene (50 ml) was heated under reflux for 1 hr. After cooling, the reaction mixture was concentrated, and the residue was purified by silica gel column chromatography (hexane:ethyl acetate=8:1, volume ratio) and recrystallized from hexane to give N-benzylidene-4-trifluoromethylbenzenecarbohydrazonoyl chloride (1.85 g, yield 59%) as pale-yellow plate crystals. melting point: 95–96° C.

Reference Example 14

To a solution (15 ml) of 2-amino-4-methoxycarbonylbenzoic acid (3.00 g) in trifluoroacetic acid was added dropwise anhydrous trifluoroacetic acid (7 ml) at 0° C. This mixture was stirred for 1 hr. and poured into water. The crystals were collected by filtration to give 4-methoxycarbonyl-2-trifluoroacetylaminobenzoic acid (4.40 g, yield 98%). Recrystallization from hexane-ethyl acetate gave colorless prism crystals. melting point: 185–186° C.

Reference Example 15

To a solution (10 ml) of 4-methoxycarbonyl-2-trifluoroacetylaminobenzoic acid (1.30 g) and N,N-dimethylformamide (0.05 ml) in tetrahydrofuran was added oxalyl chloride (0.47 ml) at 0° C. This mixture was stirred at room temperature for 1.5 hrs. and concentrated. A mixture of the residue, 4-trifluoromethyl-N-hydroxybenzeneimidoylamide (0.920 g) and N,N-dimethylacetamide (10 ml) was stirred at room temperature for 3 hrs. Water was added to the reaction mixture, and the crystals were collected by filtration and purified by silica gel column chromatography (hexane:ethyl acetate=1:1, volume ratio) to give methyl 4-[[amino[4-(trifluoromethylphenyl)]methylidene]aminooxycarbonyl]-3-trifluoroacetylaminobenzoate (1.37 g, yield 64%). Recrystallization from hexane-ethyl acetate gave colorless prism crystals. melting point: 177–178° C.

Example 1

To a solution (50 ml) of 5-chloro-2-phenylpyridine (3.50 g) in tetrahydrofuran was added dropwise t-butyl lithium (1.7 M solution in pentane, 12.0 ml) under an argon atmosphere at −78° C., and the mixture was stirred for 1 hr. To this mixed solution was added a solution (15 ml) of zinc chloride (3.00 g) in tetrahydrofuran, and the mixture was stirred at 0° C. for 30 min. Then, ethyl 4-iodobenzoate (3.4 ml) and tetrakis (triphenylphosphine)palladium (1.15 g) were added. This mixture was stirred overnight at room temperature under an argon atmosphere, and poured into 0.5 M hydrochloric acid. The mixture was extracted with ethyl acetate. The organic layer was washed with saturated aqueous sodium hydrogen carbonate solution and saturated brine, dried over anhydrous magnesium sulfate and concentrated. The residue was purified by silica gel column chromatography (hexane:ethyl acetate=9:1, volume ratio). Recrystallization from hexane-ethyl acetate gave ethyl 4-(3-chloro-6-phenyl-2-pyridyl)benzoate (3.86 g, yield 58%) as colorless crystals. melting point: 81–82° C.

Example 2

A mixture of ethyl 4-(3-chloro-6-phenyl-2-pyridyl)benzoate (1.00 g), 1M aqueous sodium hydroxide solution (5 ml), tetrahydrofuran (10 ml) and ethanol (20 ml) was stirred at 60° C. for 1 hr. After cooling, the reaction mixture was poured into water, and 1 M hydrochloric acid (5 ml) was added. The crystals were collected by filtration and recrystallized from tetrahydrofuran-hexane to give 4-(3-chloro-6-phenyl-2-pyridyl)benzoic acid (0.83 g, yield 91%) as colorless crystals. melting point: 254–255° C.

Example 3

To a solution (5 ml) of 1-methyl-2-(4-trifluoromethylphenyl)pyrrole (1.13 g) in tetrahydrofuran was added dropwise t-butyl lithium (1.7 M solution in pentane, 3.00 ml) under an argon atmosphere at −78° C. This mixed solution was heated to room temperature, and a solution (10 ml) of zinc chloride (0.756 g) in tetrahydrofuran was added. This mixture was stirred for 1 hr., and ethyl 4-iodobenzoate (0.381 ml) and tetrakis (triphenylphosphine)palladium (0.144 g) were added. This mixture was stirred overnight under an argon atmosphere and poured into 0.5 M hydrochloric acid. The mixture was extracted with ethyl acetate, and the organic layer was washed with saturated aqueous sodium hydrogen carbonate solution and saturated brine, dried over anhydrous magnesium sulfate and concentrated. The residue was purified by silica gel column chromatography (hexane:ethyl acetate=7:1, volume ratio) and recrystallized from hexane-ethyl acetate to give ethyl 4-[1-methyl-5-(4-trifluoromethylphenyl)-2-pyrrolyl]benzoate (0.573 g, yield 31%) as colorless needle crystals. melting point: 150–151° C.

Example 4

To a solution (25 ml) of 2-(4-trifluoromethylphenyl)furan (3.18 g) in tetrahydrofuran was added dropwise n-butyl lithium (1.6 M solution in hexane, 10.0 ml) under an argon atmosphere at −78° C. This mixed solution was heated to room temperature, and a solution (30 ml) of zinc chloride (2.25 g) in tetrahydrofuran was added. This mixture was stirred for 1 hr., and then ethyl 2-bromobenzoate (2.38 ml) and tetrakis (triphenylphosphine)palladium (0.433 g) were added. This mixture was stirred overnight under an argon atmosphere, and then poured into 0.5 M hydrochloric acid. The mixture was extracted with ethyl acetate. The organic layer was washed with saturated aqueous sodium hydrogen carbonate solution and saturated brine, dried over anhydrous magnesium sulfate and concentrated. The residue was purified by silica gel column chromatography (hexane:ethyl acetate=10:1, volume ratio) to give ethyl 2-[5-(4-trifluoromethylphenyl)-2-furyl]benzoate (2.54 g, yield 47%) as a pale-yellow oil. NMR (CDCl$_3$) δ: 1.12 (3H, t, J=7.2 Hz), 4.27 (2H, q, J=7.2 Hz), 6.70 (1H, d, J=3.6 Hz), 6.87 (1H, d, J=3.6 Hz), 7.41 (1H, dt, J=1.4, 7.4 Hz), 7.53 (1H, dt, J=1.4, 7.4 Hz), 7.61–7.79 (6H, m).

Example 5

To a solution (25 ml) of 2-(4-trifluoromethylphenyl)furan (3.18 g) in tetrahydrofuran was added dropwise n-butyl lithium (1.6 M solution in hexane, 10.0 ml) under an argon atmosphere at −78° C. This mixed solution was heated to room temperature, and a solution (30 ml) of zinc chloride (2.25 g) in tetrahydrofuran was added. This mixture was stirred for 1 hr., and then ethyl 3-bromobenzoate (2.38 ml) and tetrakis (triphenylphosphine)palladium (0.433 g) were added. This mixture was stirred overnight under an argon atmosphere, and then poured into 0.5 M hydrochloric acid. The mixture was extracted with ethyl acetate. The organic layer was washed with saturated aqueous sodium hydrogen carbonate solution and saturated brine, dried over anhydrous magnesium sulfate and concentrated. The residue was purified by silica gel column chromatography (hexane:ethyl acetate=5:1, volume ratio) and recrystallized from hexane-ethyl acetate to give ethyl 3-[5-(4-trifluoromethylphenyl)-2-furyl]benzoate (1.89 g, yield 35%) as pale-brown needle crystals. melting point: 93–94° C.

Example 6

To a solution (25 ml) of 2-(4-trifluoromethylphenyl)furan (3.18 g) in tetrahydrofuran was added dropwise n-butyl lithium (1.6 M solution in hexane, 10.0 ml) under an argon atmosphere at −78° C. This mixed solution was heated to room temperature, and a solution (30 ml) of zinc chloride (2.25 g) in tetrahydrofuran was added. This mixture was stirred for 1 hr., and ethyl 4-iodobenzoate (2.49 ml) and tetrakis (triphenylphosphine)palladium (0.433 g) were added. This mixture was stirred overnight under an argon atmosphere, and poured into 0.5 M hydrochloric acid. The mixture was extracted with ethyl acetate, and the organic layer was washed with saturated aqueous sodium hydrogen carbonate solution and saturated brine, dried over anhydrous magnesium sulfate and concentrated. The residue was purified by silica gel column chromatography (ethyl acetate) and recrystallized from hexane-ethyl acetate to give ethyl 4-[5-(4-triflubromethylphenyl)-2-furyl]benzoate (2.42 g, yield 45%) as colorless needle crystals. melting point: 186–187° C.

Example 7

A mixture of ethyl 4-[1-methyl-5-(4-trifluoromethyl)-2-pyrrolyl]benzoate (0.485 g), 1 M aqueous sodium hydroxide solution (5 ml), tetrahydrofuran (10 ml) and ethanol (10 ml) was stirred at 60° C. for 1 hr. After cooling, the reaction mixture was poured into water, and 1 M hydrochloric acid (10 ml) was added. The crystals were collected by filtration and recrystallized from ethanol to give 4-[1-methyl-5-(4-trifluoromethylphenyl)-2-pyrrolyl]benzoic acid (0.296 g, yield 66%) as a pale-yellow crystalline powder. melting point: 260–261° C.

Example 8

A mixture of ethyl 2-[5-(4-trifluoromethylphenyl)-2-furyl]benzoate (1.80 g), 1 M aqueous sodium hydroxide solution (20 ml), tetrahydrofuran (35 ml) and ethanol (35 ml) was stirred at 60° C. for 1 hr. After cooling, the reaction mixture was poured into water and 1 M hydrochloric acid (30 ml) was added. The mixture was extracted with ethyl acetate-tetrahydrofuran (1:1, volume ratio). The organic layer was washed with saturated brine, dried over anhydrous magnesium sulfate and concentrated. The residue was recrystallized from hexane-ethanol to give 2-[5-(4-trifluoromethylphenyl)-2-furyl]benzoic acid (1.15, yield 53%) as colorless plate crystals. melting point: 182–183° C.

Example 9

A mixture of ethyl 3-[5-(4-trifluoromethylphenyl)-2-furyl]benzoate (1.62 g), 1 M aqueous sodium hydroxide solution (10 ml), tetrahydrofuran (50 ml) and ethanol (50 ml) was stirred at 60° C. for 1 hr. After cooling, the reaction mixture was poured into water, and 1 M hydrochloric acid (20 ml) was added. Crystals were collected by filtration and recrystallized from ethanol to give 3-[5-(4-trifluoromethylphenyl)-2-furyl]benzoic acid (1.41 g, yield 95%) as a pale-yellow crystalline powder. melting point: 271–272° C.

Example 10

A mixture of ethyl 4-[5-(4-trifluoromethylphenyl)-2-furyl]benzoate (1.80 g), 1 M aqueous sodium hydroxide solution (15 ml), tetrahydrofuran (50 ml) and ethanol (50 ml) was stirred at 60° C. for 1.5 hrs. After cooling, the reaction mixture was poured into water, and 1 M hydrochloric acid (40 ml) was added. The crystals were collected by filtration and recrystallized from ethanol to give 4-[5-(4-trifluoromethylphenyl)-2-furyl]benzoic acid (1.41 g, yield 85%) as a colorless crystalline powder. melting point: 270–271° C.

Example 11

To a solution (25 ml) of 2-(4-trifluoromethylphenyl)furan (3.18 g) in tetrahydrofuran was added dropwise n-butyl lithium (1.6 M solution in hexane, 10.0 ml) under an argon atmosphere at −78° C. This mixed solution was heated to room temperature, and a solution (30 ml) of zinc chloride (2.25 g) in tetrahydrofuran was added. This mixture was stirred for 1 hr., and benzyl 2-benzyloxy-5-iodobenzoate (6.66 g) and tetrakis (triphenylphosphine)palladium (0.433 g) were added. This mixture was stirred overnight under an argon atmosphere, and poured into 0.5 M hydrochloric acid. The mixture was extracted with ethyl acetate. The organic layer was washed with saturated aqueous sodium hydrogen carbonate solution and saturated brine, dried over anhydrous magnesium sulfate and concentrated. The residue was purified by silica gel column chromatography (hexane:ethyl acetate=5:1, volume ratio) and recrystallized from hexane-ethyl acetate to give benzyl 2-benzyloxy-5-[5-(4-trifluoromethylphenyl)-2-furyl]benzoate (3.41 g, yield 43%) as pale-yellow needle crystals. melting point: 97–98° C.

Example 12

A mixture of benzyl 2-benzyloxy-5-[5-(4-trifluromethylphenyl)-2-furyl]benzoate (2.64 g), 5% palladium on carbon (2.6 g), tetrahydrofuran (50 ml) and methanol (50 ml) was stirred under a hydrogen atmosphere at normal pressure and room temperature for 30 min. Palladium on carbon was removed by filtration, and the filtrate was concentrated. The residue was recrystallized from ethanol to give 5-[5-(4-trifluoromethylphenyl)-2-furyl]salicylic acid (1.07 g, yield 62%) as a colorless crystalline powder. melting point: 272–273° C.

Example 13

To a solution (15 ml) of 2-(4-chlorophenyl)thiophene (2.63 g) in tetrahydrofuran was added dropwise n-butyl lithium (1.6 M solution in hexane, 9.00 ml) under an argon atmosphere at −78° C. This mixed solution was heated to room temperature, and a solution (30 ml) of zinc chloride (2.04 g) in tetrahydrofuran was added. This mixture was stirred for 1 hr., and ethyl 4-iodobenzoate (1.16 ml) and tetrakis(triphenylphosphine)palladium (0.202 g) were added. This mixture was stirred overnight under an argon atmosphere, and poured into 0.5 M hydrochloric acid. The mixture was extracted with ethyl acetate. The organic layer was washed with saturated aqueous sodium hydrogen carbonate solution and saturated brine, dried over anhydrous magnesium sulfate and concentrated. Ethanol (200 ml) was added to the residue, and the mixture was heated under reflux for 10 min. Insoluble materials were filtered off, and the filtrate was concentrated to give ethyl 4-[5-(4-chlorophenyl)-2-thienyl]benzoate (2.42 g, yield 45%) as a pale-green crystalline powder. melting point: 167–168° C.

Example 14

To a solution (7 ml) of 2-(4-trifluoromethylphenyl)thiophene (1.71 g) in tetrahydrofuran was added dropwise n-butyl lithium (1.6 M solution in hexane, 5.00 ml) under an argon atmosphere at −78° C. This mixed solution was heated to room temperature, and a solution (14 ml) of zinc chloride (1.09 g) in tetrahydrofuran was added. This mixture was stirred for 1 hr., and ethyl 4-iodobenzoate (1.16 ml) and tetrakis(triphenylphosphine)palladium (0.202 g) were added. This mixture was stirred overnight under an argon atmosphere and poured into 0.5 M hydrochloric acid. The mixture was extracted with ethyl acetate. The organic layer was washed with saturated aqueous sodium hydrogen carbonate solution and saturated brine, dried over anhydrous magnesium sulfate and concentrated. Ethanol (200 ml) was added to the residue, and the mixture was heated under reflux for 10 min. Insoluble materials were filtered off, and the filtrate was concentrated to give ethyl 4-[5-(4-trifluoromethylphenyl)-2-thienyl]benzoate (1.19 g, yield 45%) as a yellow crystalline powder. melting point: 203–204° C.

Example 15

A mixture of ethyl 4-[5-(4-chlorophenyl)-2-thienyl]benzoate (1.03 g), 1 M aqueous sodium hydroxide solution (4.5 ml), tetrahydrofuran (30 ml) and ethanol (30 ml) was stirred at 60° C. for 1.5 hrs. After cooling, the reaction mixture was poured into water, and 1 M hydrochloric acid (15 ml) was added. The crystals were collected by filtration and recrystallized from ethanol to give 4-[5-(4-chlorophenyl)-2-thienyl]benzoic acid (0.566 g, yield 60%) as a pale-green crystalline powder. melting point: 285–286° C.

Example 16

A mixture of ethyl 4-[5-(4-trifluoromethylphenyl)-2-thienyl]benzoate (0.941 g), 1 M aqueous sodium hydroxide solution (7.5 ml), tetrahydrofuran (25 ml) and ethanol (25 ml) as stirred at 60° C. for 1 hr. After cooling, the reaction mixture was poured into water, and 1 M hydrochloric acid (25 ml) was added. The crystals were collected by filtration and recrystallized from ethanol to give 4-[5-(4-trifluoromethylphenyl)-2-thienyl]benzoic acid (0.583 g, yield 67%) as a yellow crystalline powder. melting point: 284–285° C.

Example 17

To a solution (100 ml) of N-hydroxybenzenimidoyl chloride (2.25 g) and methyl 4-ethynylbenzoate (2.30 g) in tetrahydrofuran was added dropwise a solution (10 ml) of triethylamine (2.30 ml) in tetrahydrofuran under an argon atmosphere at 0° C. This mixture was stirred overnight at room temperature and poured into water. The mixture was extracted with ethyl acetate. The organic layer was washed with water and saturated brine, dried over anhydrous magnesium sulfate and concentrated. The residue was recrystallized from hexane-tetrahydrofuran to give methyl 4-(3-phenyl-5-isoxazolyl)benzoate (3.49 g, yield 87%) as colorless crystals. melting point: 205–206° C.

Example 18

To a solution (70 ml) of 4-chloro-N-hydroxybenzenimidoyl chloride (3.28 g) and methyl 4-ethynylbenzoate (3.00 g) in tetrahydrofuran was added dropwise a solution (5 ml) of triethylamine (2.8 ml) in tetrahydrofuran under an argon atmosphere at 0° C. This mixture was stirred overnight at room temperature and poured into dilute hydrochloric acid. The mixture was extracted with ethyl acetate. The organic layer was washed with saturated brine, dried over anhydrous magnesium sulfate and concentrated. The residue was purified by silica gel column chromatography (hexane:ethyl acetate=1:1, volume ratio) to give methyl 4-[3-(4-chlorophenyl)-5-isoxazolyl]benzoate (4.40 g, yield 81%). Recrystallization from hexane-acetone gave colorless prism crystals. melting point: 225–226° C.

Example 19

To a solution (30 ml) of 4-trifluoromethyl-N-hydrobenzenimidoyl chloride (1.50 g) and methyl 4-ethynylbenzoate (1.20 g) in tetrahydrofuran was added dropwise a solution (5 ml) of triethylamine (2.0 ml) in tetrahydrofuran under an argon atmosphere at 0° C. This mixture was stirred overnight at room temperature, and poured into dilute hydrochloric acid. The mixture was extracted with ethyl acetate. The organic layer was washed with saturated brine, dried over anhydrous magnesium sulfate and concentrated. The residue was recrystallized from hexane-tetrahydrofuran to give methyl 4-[3-(4-trifluorophenyl)-5-isoxazolyl]benzoate (2.09 g, yield 90%) as colorless crystals. melting point: 192–193° C.

Example 20

To a solution (40 ml) of methyl 3-[chloro(hydroxyimino)methyl]benzoate (1.42 g) and ethynylbenzene (1.0 ml) in tetrahydrofuran was added dropwise a solution (10 ml) of triethylamine (2.5 ml) in tetrahydrofuran under an argon atmosphere at 0° C. This mixture was stirred overnight at room temperature and poured into water. The mixture was extracted with ethyl acetate. The organic layer was washed with water and saturated brine, dried over anhydrous magnesium sulfate and concentrated. The residue was recrystallized from hexane-ethyl acetate to give methyl 3-(5-phenyl-3-isoxazolyl)benzoate. (2.43 g, yield 96%) as colorless crystals. melting point: 99–100° C.

Example 21

To a solution (70 ml) of methyl 4-[chloro(hydroxyimino)methyl]benzoate (2.20 g) and ethynylbenzene (1.3 ml) in tetrahydrofuran was added dropwise a solution (10 ml) of triethylamine (3.0 ml) in tetrahydrofuran under an argon atmosphere at 0° C. This mixture was stirred overnight at room temperature and poured into water. The mixture was extracted with ethyl acetate. The organic layer was washed with water and saturated brine, dried over anhydrous magnesium sulfate and concentrated. The residue was recrystallized from hexane-tetrahydrofuran to give methyl 4-(5-phenyl-3-isoxazolyl)benzoate (2.47 g, yield 86%) as colorless crystals. melting point: 201–202° C.

Example 22

To a solution (50 ml) of methyl 3-[chloro(hydroxyimino)methyl]benzoate (1.65 g) and ethynylbenzene (1.05 g) in tetrahydrofuran was added dropwise a solution (10 ml) of triethylamine (2.5 ml) in tetrahydrofuran under an argon atmosphere at 0° C. This mixture was stirred overnight at room temperature and poured into water. The mixture was extracted with ethyl acetate. The organic layer was washed with water and saturated brine, dried over anhydrous magnesium sulfate and concentrated. The residue was recrystallized from hexane-tetrahydrofuran to give methyl 3-[5-(4-chlorophenyl)-3-isoxazolyl)benzoate (2.08 g, yield 86%) as colorless crystals. melting point: 157–158° C.

Example 23

To a solution (70 ml) of methyl 4-[chloro(hydroxyimino)methyl]benzoate (1.65 g) and 4-chloro-ethynylbenzene (1.06 g) in tetrahydrofuran was added dropwise a solution (10 ml) of triethylamine (2.5 ml) in tetrahydrofuran under an argon atmosphere at 0° C. This mixture was stirred overnight at room temperature and poured into water. The mixture was extracted with ethyl acetate. The organic layer was washed with water and saturated brine, dried over anhydrous magnesium sulfate and concentrated. The residue was recrystallized from hexane-tetrahydrofuran to give methyl 4-[5-(4-chlorophenyl)-3-isoxazolyl]benzoate (2.20 g, yield 91%) as colorless crystals. melting point: 225–226° C.

Example 24

A mixture of methyl 4-(3-phenyl-5-isoxazolyl)benzoate (1.70 g), 1 M aqueous sodium hydroxide solution (10 ml), tetrahydrofuran (30 ml) and methanol (30 ml) was stirred at 60° C. for 1 hr. After cooling, the reaction mixture was poured into water, and 1 M hydrochloric acid (10 ml) was added. The crystals were collected by filtration and recrystallized from N,N-dimethylformamide-water to give 4-(3-phenyl-5-isoxazolyl)benzoic acid (1.56 g, yield 97%) as colorless crystals. melting point: >300° C.

Example 25

A mixture of methyl 4-[3-(4-chlorophenyl)-5-isoxazolyl]benzoate (1.50 g), conc. hydrochloric acid (30 ml) and acetic acid (100 ml) was heated under reflux for 5 hrs. After cooling, the reaction mixture was poured into water and the crystals were washed with water to give 4-[3-(4-chlorophenyl)-5-isoxazolyl]benzoic acid (1.38 g, yield 97%). Recrystallization from N,N-dimethylformamide-water gave colorless prism crystals. melting point: >300° C.

Example 26

A mixture of methyl 4-[3-(4-trifluorophenyl)-5-isoxazolyl]benzoate (1.50 g), 1 M aqueous sodium hydroxide solution (10 ml), tetrahydrofuran (30 ml) and methanol (10 ml) was stirred at 60° C. for 1 hr. After cooling, the reaction mixture was poured into water and 1 M hydrochloric acid (10 ml) was added. The crystals were collected by filtration and recrystallized from tetrahydrofuran-hexane to give 4-[3-(4-trifluorophenyl)-5-isoxazolyl]benzoic acid (1.39 g, yield 97%) as colorless crystals. melting point: >300° C.

Example 27

A mixture of methyl 3-(5-phenyl-3-isoxazolyl)benzoate (1.30 g), 1 M aqueous sodium hydroxide solution (10 ml), tetrahydrofuran (20 ml) and methanol (10 ml) was stirred at 60° C. for 1 hr. After cooling, the reaction mixture was poured into water, and 1 M hydrochloric acid (10 ml) was added. The crystals were collected by filtration and recrystallized from tetrahydrofuran-hexane to give 3-(5-phenyl-3-isoxazolyl)benzoic acid (1.05 g, yield 85%) as colorless crystals. melting point: 250–251° C.

Example 28

A mixture of methyl 4-(5-phenyl-3-isoxazolyl)benzoate (1.05 g), 6 M hydrochloric acid (10 ml) and acetic acid (20 ml) was heated under reflux for 5 hrs. After cooling, the reaction mixture was poured into water, and the crystals were washed with water to give 4-(5-phenyl-3-isoxazolyl) benzoic acid (0.95 g, yield 95%). Recrystallization from N,N-dimethylformamide-water gave colorless prism crystals. melting point: 297–298° C.

Example 29

A mixture of methyl 3-[5-(4-chlorophenyl)-3-isoxazolyl]benzoate (1.10 g), 1 M aqueous sodium hydroxide solution (5 ml), tetrahydrofuran (15 ml) and methanol (15 ml) was stirred at 60° C. for 1 hr. After cooling, the reaction mixture was poured into water, and 1 M hydrochloric acid (5 ml) was added. The crystals were collected by filtration and recrystallized from tetrahydrofuran-hexane to give 3-[5-(4-chlorophenyl)-3-isoxazolyl]benzoic acid (0.91 g, yield 87%) as colorless crystals. melting point: 298–299° C.

Example 30

A mixture of methyl 4-[5-(4-chlorophenyl)-3-isoxazolyl]benzoate (1.35 g), 1 M aqueous sodium hydroxide solution (10 ml), tetrahydrofuran (20 ml) and methanol (10 ml) was stirred at 60° C. for 1 hr. After cooling, the reaction mixture was poured into water, and 1 M hydrochloric acid (10 ml) was added. The crystals were collected by filtration, and recrystallized from tetrahydrofuran-hexane to give 4-[5-(4-chlorophenyl)-3-isoxazolyl]benzoic acid (1.19 g, yield 92%) as colorless crystals. melting point: >300° C.

Example 31

To a solution (60 ml) of methyl 3-[chloro(hydroxyimino)methyl]benzoate (2.14 g) and 1-ethynyl-4-trifluoromethylbenzene (1.73 g) in tetrahydrofuran was added dropwise a solution (40 ml) of triethylamine(2.79 ml) in tetrahydrofuran under an argon atmosphere at 0° C. This mixture was stirred overnight at room temperature and poured into water. The mixture was extracted with ethyl acetate. The organic layer was washed with water and saturated brine, dried over anhydrous magnesium sulfate and concentrated. The residue was recrystallized from hexane-ethyl acetate to give methyl 3-[5-(4-trifluoromethylphenyl)-3-isoxazolyl]benzoate (1.64 g, yield 47%) as a colorless crystalline powder. melting point: 139–140° C.

Example 32

To a solution (15 ml) of methyl 4-[chloro(hydroxyimino)methyl]benzoate (0.425 g) and 1-ethynyl-4-trifluoromethylbenzene (0.534 g) in tetrahydrofuran was added dropwise a solution (10 ml) of triethylamine (0.697 ml) in tetrahydrofuran under an argon atmosphere at 0° C. This mixture was stirred overnight at room temperature and poured into water. The mixture was extracted with ethyl acetate. The organic layer was washed with water and saturated brine, dried over anhydrous magnesium sulfate and concentrated. The residue was recrystallized from hexane-ethyl acetate to give methyl 4-[5-(4-trifluoromethylphenyl)-3-isoxazolyl]benzoate (0.563 g, yield 65%) as colorless needle crystals. melting point: 183–184° C.

Example 33

To a mixture of 3-[3-(4-trifluoromethylphenyl)-5-isoxazolyl]benzaldehyde (0.539 g), sodium dihydrogen phosphate (0.204 g), 2-methyl-2-butene (1.80 ml), acetonitrile (40 ml) and water (10 ml) was added an aqueous solution (5 ml) of sodium chlorite (0.769 g), and the mixture was stirred at room temperature for 1 hr. To this mixture was added sodium sulfite (1.5 g), and the mixture was stirred for 10 min. and poured into 1 M hydrochloric acid. The crystals were collected by filtration and recrystallized from ethanol to give 3-[3-(4-trifluoromethylphenyl)-5-isoxazolyl]benzoic acid (0.451 g, yield 80%) as a colorless crystalline powder. melting point: 272–273° C.

Example 34

A mixture of methyl 3-[5-(4-trifluoromethylphenyl)-3-isoxazolyl]benzoate (1.04 g), 1 M aqueous sodium hydroxide solution (10 ml), tetrahydrofuran (30 ml) and methanol (30 ml) was stirred at 60° C. for 1 hr. After cooling, the reaction mixture was poured into water, and 1 M hydrochloric acid (20 ml) was added. The crystals were collected by filtration and recrystallized from ethanol to give 3-[5-(4-trifluoromethylphenyl)-3-isoxazolyl]benzoic acid (0.876 g, yield 88%) as a colorless crystalline powder. melting point: 276–277° C.

Example 35

A mixture of methyl 4-[5-(4-trifluoromethylphenyl)-3-isoxazolyl]benzoate (0.486 g), 1 M aqueous sodium hydroxide solution (4 ml), tetrahydrofuran (20 ml) and methanol (20 ml) was stirred at 60° C. for 1 hr. After cooling, the reaction mixture was poured into water and 1 M hydrochloric acid (15 ml) was added. The crystals were collected by filtration and recrystallized from ethanol to give 4-[5-(4-trifluoromethylphenyl)-3-isoxazolyl]benzoic acid (0.358 g, yield 77%) as a colorless crystalline powder. melting point: >300° C.

Example 36

To a solution (30 ml) of methyl benzimidate hydrochloride (3.00 g) in methanol was added hydrazine monohydrate (0.880 g) at 0° C. This mixture was stirred at 0° C. for 1 hr. and at room temperature for 2 hrs. and concentrated. A mixture of the residue, methyl 4-chloroformylbenzoate (3.48 g) and pyridine (30 ml) was heated under reflux for 2 hrs. After cooling, the reaction mixture was poured into water. The mixture was extracted with ethyl acetate. The organic layer was washed with water and saturated brine, dried over anhydrous magnesium sulfate and concentrated. The residue was purified by silica gel column chromatography (hexane:tetrahydrofuran=3:1, volume ratio) to give methyl 4-(5-phenyl-1H-1,2,4-triazol-3-yl)benzoate (1.02 g, yield 21%). Recrystallization from hexane-tetrahydrofuran gave colorless prism crystals. melting point: 243–244° C.

Example 37

To a solution (20 ml) of methyl benzimidate hydrochloride (2.00 g) in methanol was added methylhydrazine (0.540 g) at 0° C. This mixture was stirred at 0° C. for 1 hr., and at room temperature for 2 hrs., and concentrated. The residue was washed with ether to give colorless crystals. A mixture of these crystals, methyl 4-chloroformylbenzoate (2.32 g) and pyridine (30 ml) was heated under reflux for 1 hr. and poured into iced water. The crystals were collected by filtration and purified by silica gel column chromatography (hexane:ethyl acetate=2:1, volume ratio) to give methyl 4-(1-methyl-5-phenyl-1H-1,2,4-triazol-3-yl)benzoate (1.50 g, yield 44%). Recrystallization from hexane-ethyl acetate gave colorless prism crystals. melting point: 167–168° C.

Example 38

A mixture of methyl 4-(5-phenyl-1H-1,2,4-triazol-3-yl) benzoate (0.500 g), 1 M aqueous sodium hydroxide solution (5.4 ml), tetrahydrofuran (6 ml) and methanol (3 ml) was stirred at room temperature for 2 hrs. and heated under reflux for 2 hrs. After cooling, 1 M hydrochloric acid was added to acidify the reaction mixture. The crystals were collected by filtration to give 4-(5-phenyl-1H-1,2,4-triazol-3-yl)benzoic acid (0.380 g, yield 79%). Recrystallization from hexane-tetrahydrofuran gave colorless prism crystals. melting point: >300° C.

Example 39

A mixture of methyl 4-(1-methyl-5-phenyl-1H-1,2,4-triazol-3-yl)benzoate (0.700 g), 1 M aqueous sodium hydroxide solution (4.8 ml), tetrahydrofuran (10 ml) and methanol (5 ml) was stirred at room temperature for 2 hrs., and acidified by adding 1 M hydrochloric acid. The crystals were collected by filtration to give 4-(1-methyl-5-phenyl-1H-1,2,4-triazol-3-yl)benzoic acid (0.650 g, yield 97%). Recrystallization from hexane-tetrahydrofuran gave colorless prism crystals. melting point: 243–244° C.

Example 40

A mixture of methyl 4-chloroformylbenzoate (1.95 g), 4-trifluoromethylphenyl amidoxime (2.00 g) and pyridine (25 ml) was heated under reflux for 1 hr. After cooling, water was added to the mixture. The crystals were collected by filtration and purified by silica gel column chromatography (hexane:tetrahydrofuran=1:9, volume ratio) to give methyl 4-[3-(4-trifluoromethylphenyl)-1,2,4-oxadiazol-5-yl]benzoate (2.98 g, yield 87%). Recrystallization from hexane-tetrahydrofuran gave colorless crystals. melting point: 177–178° C.

Example 41

A mixture of methyl 4-chloroformylbenzoate (2.70 g), 4-phenoxyphenyl amidoxime (3.08 g) and pyridine (30 ml) was heated under reflux for 1 hr. After cooling, water was added to the mixture. The crystals were collected by filtration and purified by silica gel column chromatography (hexane:tetrahydrofuran=1:9, volume ratio) to give methyl 4-[3-(4-phenoxyphenyl)-1,2,4-oxadiazol-5-yl]benzoate (4.63 g, yield 92%). Recrystallization from hexane-ethyl acetate gave colorless crystals. melting point: 112–113° C.

Example 42

A mixture of methyl 4-[3-(4-trifluoromethylphenyl)-1,2,4-oxadiazol-5-yl]benzoate (2.10 g), 1 M aqueous sodium hydroxide solution (12 ml), tetrahydrofuran (20 ml) and methanol (20 ml) was stirred at 60° C. for 1 hr. The mixture was acidified by adding 1 M hydrochloric acid. The crystals were collected by filtration to give 4-[3-(4-trifluoromethylphenyl)-1,2,4-oxadiazol-5-yl]benzoic acid (1.82 g, yield 90%). Recrystallization from hexane-tetrahydrofuran gave colorless crystals. melting point: 293–294° C.

Example 43

A mixture of methyl 4-[3-(4-phenoxyphenyl)-1,2,4-oxadiazol-5-yl]benzoate (1.50 g), 1 M aqueous sodium hydroxide solution (8 ml), tetrahydrofuran (10 ml) and methanol (10 ml) was stirred at 60° C. for 1 hr. and acidified by adding 1 M hydrochloric acid. The crystals were collected by filtration to give 4-[3-(4-phenoxyphenyl)-1,2,4-oxadiazol-5-yl]benzoic acid (1.31 g, yield 91%). Recrystallization from hexane-tetrahydrofuran gave colorless crystals. melting point: 278–279° C.

Example 44

To a mixture of 4-[5-(4-trifluoromethylphenyl)-1,2,4-oxadiazol-3-yl]benzaldehyde (1.30 g), sodium dihydrogen phosphate (0.51 g), 2-methyl-2-butene (1.3 ml), water (15 ml), t-butanol (15 ml) and tetrahydrofuran (30 ml) was slowly added sodium chlorite (0.75 g) at 0° C., and the mixture was stirred for 2 hrs. To the reaction mixture was added conc. hydrochloric acid (3 ml), and the mixture was extracted with ethyl acetate. The ethyl acetate layer was washed with saturated brine, dried over anhydrous magnesium sulfate and concentrated. The obtained colorless crystals were recrystallized from tetrahydrofuran-hexane to give 4-[5-(4-trifluoromethylphenyl)-1,2,4-oxadiazol-3-yl]benzoic acid (1.21 g, yield 89%). melting point: 286–287° C.

Example 45

A mixture of methyl 4-chloroformylbenzoate (6.81 g), 5-phenyl-1H-tetrazole (5.01 g) and pyridine (10 ml) was heated under reflux for 1 hr. After cooling, water was added to the mixture. The crystals were collected by filtration, and dissolved in ethyl acetate. This solution was washed with 1 M hydrochloric acid, water and saturated brine, dried over anhydrous magnesium sulfate and concentrated. The residue was washed with cold hexane to give methyl 4-(5-phenyl-1,3,4-oxadiazol-2-yl)benzoate (7.88 g, yield 82%). Recrystallization from hexane-tetrahydrofuran gave colorless crystals. melting point: 172–173° C.

Example 46

A mixture of methyl 4-chloroformylbenzoate (1.39 g), 5-(4-trifluoromethylphenyl)-1H-tetrazol (1.50 g) and pyridine (30 ml) was heated under reflux for 1 hr. After cooling, water was added to the mixture. The crystals were collected by filtration and purified by silica gel column chromatography (hexane:tetrahydrofuran=1:9, volume ratio) to give methyl 4-[5-(4-trifluoromethylphenyl)-1,3,4-oxadiazol-2-yl]benzoate (1. 85 g, yield 76%). Recrystallization from hexane-ethyl acetate gave colorless prism crystals. melting point: 216–217° C.

Example 47

A mixture of methyl 4-chloroformylbenzoate (1.17 g), 5-(4-t-butylphenyl)-1H-tetrazole (1.00 g) and pyridine (10 ml) was heated under reflux for 1 hr. After cooling, water was added to the mixture. The crystals were collected by filtration and dissolved in ethyl acetate. This solution was washed with 1 M hydrochloric acid, water and saturated brine, dried over anhydrous magnesium sulfate and concentrated. The residue was washed with cold hexane to give methyl 4-[5-(4-t-butylphenyl)-1,3,4-oxadiazol-2-yl]benzoate (1.51, yield 92%). Recrystallization from hexane-tetrahydrofuran gave colorless prism crystals. melting point: 210–211° C.

Example 48

A mixture of methyl 4-[5-phenyl-1,3,4-oxadiazol-2-yl]benzoate (0.180 g), 1 M aqueous sodium hydroxide solution (1.3 ml), tetrahydrofuran (2 ml) and methanol (1 ml) was stirred at room temperature for 1 hr. and acidified by adding 1 M hydrochloric acid. The crystals were collected by filtration to give 4-[5-phenyl-1,3,4-oxadiazol-2-yl]benzoic acid (0.150 g, yield 88%). Recrystallization from hexane-tetrahydrofuran gave colorless prism crystals. melting point: >300° C.

Example 49

A mixture of methyl 4-[5-(4-trifluoromethylphenyl)-1,3,4-oxadiazol-2-yl]benzoate (0.800 g), 1 M aqueous sodium hydroxide solution (4.6 ml) and tetrahydrofuran (5 ml) was heated under reflux for 1.5 hrs. After cooling, 1 M hydrochloric acid was added to acidify the mixture. The crystals were collected by filtration to give 4-[5-(4-trifluoromethylphenyl)-1,3,4-oxadiazol-2-yl]benzoic acid (0.71 g, yield 92%). Recrystallization from hexane-ethyl acetate gave colorless prism crystals. melting point: >300° C.

Example 50

A mixture of methyl 4-[5-(4-t-butylphenyl)-1,3,4-oxadiazol-2-yl]benzoate (0.600 g), 1 M aqueous sodium hydroxide solution (3.6 ml), tetrahydrofuran (6 ml) and ethanol (3 ml) was heated under reflux for 1.5 hrs. After cooling, 1 M hydrochloric acid was added to acidify the mixture. The crystals were collected by filtration to give 4-[5-(4-t-butylphenyl)-1,3,4-oxadiazol-2-yl]benzoic acid (0.550 g, yield 95%). Recrystallization from hexane-tetrahydrofuran gave colorless prism crystals. melting point: 284–286° C.

Example 51

To a mixture of 3-[5-(4-trifluoromethylphenyl)-1,3,4-oxadiazol-2-yl]benzaldehyde (0.800 g), sodium dihydrogen phosphate (0.300 g), 2-methyl-2-butene (1.2 ml), t-butanol (10 ml), tetrahydrofuran (20 ml) and water (10 ml) was added sodium chlorite (0.570 g) at 0° C., and the mixture was stirred for 2 hrs. To the mixture was added aqueous sodium sulfite solution, and the mixture was stirred at room temperature for 30 min., acidified by adding 1 M hydrochloric acid, and extracted with ethyl acetate-tetrahydrofuran. The organic layer was washed with water and saturated brine, dried over anhydrous magnesium sulfate, and concentrated to give 3-[5-(4-trifluoromethylphenyl)-1,3,4-oxadiazol-2-yl]benzoic acid (0.730 g, yield 87%). Recrystallization from hexane-tetrahydrofuran gave colorless prism crystals. melting point: 239–240° C.

Example 52

To a mixture of 4-[5-(2-nitrophenyl)-1,3,4-oxadiazol-2-yl]benzaldehyde (0.930 g), sodium dihydrogen phosphate (0.490 g), 2-methyl-2-butene (1.95 ml), t-butanol (20 ml), tetrahydrofuran (20 ml) and water (20 ml) was added sodium chlorite (0.570 g) at 0° C., and the mixture was stirred for 3 hrs. To the mixture was added an aqueous sodium sulfite solution, and the mixture was stirred at room temperature for 15 min., and acidified by adding 1 M hydrochloric acid. The crystals were collected by filtration to give 4-[5-(2-nitrophenyl)-1,3,4-oxadiazol-2-yl]benzoic acid (1.00 g, yield 78%). Recrystallization from hexane-tetrahydrofuran gave pale-yellow prism crystals. melting point: 239–240° C.

Example 53

A mixture of 4-[5-(2-nitrophenyl)-1,3,4-oxadiazol-2-yl]benzoic acid (2.00 g), conc. sulfuric acid (0.5 ml) and ethanol (50 ml) was heated under reflux for 6 hrs. After cooling, the reaction mixture was concentrated, and the residue was diluted with ethyl acetate. This solution was washed with saturated aqueous sodium hydrogen carbonate solution and saturated brine, dried over anhydrous magnesium sulfate and concentrated. The residue was purified by silica gel column chromatography (hexane:ethyl acetate=4:1-2:1, volume ratio) to give ethyl 4-[5-(2-nitrophenyl)-1,3,4-oxadiazol-2-yl]benzoate (0.51 g, yield 24%). Recrystallization from hexane-ethyl acetate gave pale-yellow prism crystals. melting point: 127–128° C.

Example 54

A mixture of ethyl 4-[5-(2-nitrophenyl)-1,3,4-oxadiazol-2-yl]benzoate (2.00 g), 5%.palladium on carbon (0.4 g) and tetrahydrofuran (50 ml) was stirred under a hydrogen atmosphere at room temperature and normal pressure for 30 min. Palladium on carbon was filtered off, and the filtrate was concentrated. The residue was purified by silica gel column chromatography (hexane:ethyl acetate=9:1, volume ratio) to give ethyl 4-[5-(2-aminophenyl)-1,3,4-oxadiazol-2-yl]benzoate (0.23 g, yield 62%). Recrystallization from hexane-ethyl acetate gave pale-yellow prism crystals. melting point: 174–175° C.

Example 55

A mixture of ethyl 4-[5-(2-aminophenyl)-1,3,4-oxadiazol-2-yl]benzoate (0.17 g),. 1 M aqueous sodium hydroxide solution (1.1 ml) and tetrahydrofuran (2 ml) was heated under reflux for 30 min. After cooling, 1 M hydrochloric acid was added to acidify the mixture. The crystals were collected by filtration to give 4-[5-(2-aminophenyl)-1,3,4-oxadiazol-2-yl]benzoic acid (0.13 g, yield 87%). Recrystallization from hexane-tetrahydrofuran gave colorless prism crystals. melting point: >300° C.

Example 56

To a solution (50 ml) of 2-methoxycarbonylbenzoic acid (2.0 g) and N,N-dimethylformamide (0.05 ml) in tetrahydrofuran was added oxalyl chloride (1.16 ml) at 0° C. This mixture was stirred at room temperature for 1.5 hrs., and concentrated. A mixture of the residue, 5-(4-t-butylphenyl)-1H-tetrazole (2.25 g) and pyridine (30 ml) was heated under reflux for 1 hr. After cooling, water was added to the reaction mixture, and the mixture was extracted with ethyl acetate. The organic layer was washed with 1 M hydrochloric acid, water and saturated brine, dried over anhydrous magnesium sulfate and concentrated. The residue was purified by silica gel column chromatography (hexane:ethyl acetate=9:1, volume ratio) to give methyl 2-[5-(4-t-butylphenyl)-1,3,4-oxadiazol-2-yl]benzoate (2.90 g, yield 78%) as a colorless oil. NMR (CDCl$_3$) δ: 1.37 (9H, s), 3.84 (3H, s), 7.51–7.72 (4H, m), 7.90–8.04 (2H, m).

Example 57

A mixture of methyl 2-[5-(4-t-butylphenyl)-1,3,4-oxadiazol-2-yl]benzoate (1.50 g), 1 M aqueous sodium hydroxide solution (9.0 ml), tetrahydrofuran (18 ml) and methanol (9 ml) was heated under reflux for 1 hr. After cooling, 1 M hydrochloric acid was added to acidify the mixture, and the mixture was extracted with ethyl acetate. The organic layer was washed with water and saturated brine, dried over anhydrous magnesium sulfate, and concentrated to give 2-[5-(4-t-butylphenyl)-1,3,4-oxadiazol-2-yl]benzoic acid (1.26 g, yield 87%) as a colorless amorphous solid. NMR (CDCl$_3$) δ: 1.35 (9H, s), 7.52 (2H, d, J=8.8 Hz), 7.67–7.76 (4H, m), 7.96–8.04 (3H, m), 8.15–8.20 (1H, m).

Example 58

A mixture of N-benzylidene-4-trifluoromethylbenzenecarbohydrazonoyl chloride (1.55 g), methyl 4-thiocarbamoylbenzoate (0.976 g) and methanol (50 ml) was stirred at 50° C. for 2 hrs. After cooling, the crystals were collected by filtration to give methyl 4-[5-(4-trifluoromethylphenyl)-1,3,4-thiadiazol-2-yl]benzoate (1.03 g, yield 57%) as a colorless crystalline powder. melting point: 218–219° C.

Example 59

A mixture of methyl 4-[5-(4-trifluoromethylphenyl)-1,3,4-thiadiazol-2-yl]benzoate (0.838 g), 1 M aqueous sodium hydroxide solution (5 ml), tetrahydrofuran (100 ml) and methanol (50 ml) was heated under reflux for 1 hr. After cooling, the reaction mixture was poured into water, and 1 M hydrochloric acid was added to acidify the mixture. The mixture was extracted with ethyl acetate-tetrahydrofuran (1:1, volume ratio). The organic layer was washed with water and saturated brine, dried over anhydrous magnesium sulfate and concentrated. The residue was recrystallized from tetrahydrofuran to give 4 [5-(4-trifluoromethylphenyl)-1,3,4-thiadiazol-2-yl]benzoic acid (0.672 g, yield 83%) as a colorless crystalline powder. melting point: >300° C.

Example 60

To a solution (50 ml) of 2-nitro-4-methoxycarbonylbenzoic acid (3.31 g) and N,N-dimethylformamide (0.05 ml) in tetrahydrofuran was added oxalyl chloride (1.54 ml) at 0° C. This mixture was stirred at room temperature for 1.5 hrs., and concentrated. A mixture of the residue, 4-chloro-N-hydroxybenzenimidoylamide (2.50 g) and pyridine (30 ml) was heated under reflux for 1 hr. After cooling, water was added to the reaction mixture, and crystals were collected by filtration and dissolved in ethyl acetate. The solution was washed with 1 M hydrochloric acid, water and saturated brine, dried over anhydrous magnesium sulfate and concentrated. The residue was purified by silica gel column chromatography (hexane:ethyl acetate=6:1, volume ratio) to give methyl 4-[3-(4-chlorophenyl)-1,2,4-oxadiazol-5-yl]-3-nitrobenzoate (2.55 g, yield 48%). Recrystallization from hexane-ethyl acetate gave colorless prism crystals. melting point: 189–190° C.

Example 61

To a solution (150 ml) of 2-nitro-4-methoxycarbonylbenzoic acid (5.00 g) and N,N-dimethylformamide (0.05 ml) in tetrahydrofuran was added oxalyl chloride (2.13 ml) at 0° C. This mixture was stirred at room temperature for 1.5 hrs., and concentrated. A mixture of the residue, 4-trifluoromethyl-N-hydroxybenzeneimidoylamide (4.53 g) and pyridine (100 ml) was heated under reflux for 1 hr. After cooling, water was added to the reaction mixture, and the crystals were collected by filtration and dissolved in ethyl acetate. The solution was washed with 1 M hydrochloric acid, water and saturated brine, dried over anhydrous magnesium sulfate and concentrated. The residue was purified by silica gel column chromatography (hexane:ethyl acetate=6:1, volume ratio) to give methyl 3-nitro-4-[3-(4-trifluoromethylphenyl)-1,2,.4-oxadiazol-5-yl]benzoate (4.74 g, yield 54%). Recrystallization from hexane-ethyl acetate gave colorless prism crystals. melting point: 146–147° C.

Example 62

A mixture of methyl 4-[3-(4-chlorophenyl)-1,2,4-oxadiazol-5-yl]-3-nitrobenzoate (1.20 g), 1 M aqueous sodium hydroxide solution (6.6 ml) and tetrahydrofuran (10 ml) was heated under reflux for 30 min. After cooling, the reaction mixture was poured into water, and 1 M hydrochloric acid was added to acidify the mixture. The crystals were collected by filtration to give 4-[3-(4-chlorophenyl)-1,2,4-oxadiazol-5-yl]-3-nitrobenzoic acid (1.10 g, yield 96%). Recrystallization from hexane-tetrahydrofuran gave colorless prism crystals. melting point: 257–258° C.

Example 63

A mixture of methyl 3-nitro-4-[3-(4-trifluoromethylphenyl)-1,2,4-oxadiazol-5-yl]benzoate (2.00 g), 1 M aqueous sodium hydroxide solution (10.2 ml) and tetrahydrofuran (10 ml) was heated under reflux for 1 hr. After cooling, 1 M hydrochloric acid was added to acidify the reaction mixture. The crystals were collected by filtration to give 3-nitro-4-[3-(4-trifluoromethylphenyl)-1,2,4-oxadiazol-5-yl]benzoic acid (1.84 g, yield 95%). Recrystallization from hexane-tetrahydrofuran gave pale-yellow prism crystals. melting point: 233–234° C.

Example 64

A mixture of 4-[3-(4-chlorophenyl)-1,2,4-oxadiazol-5-yl]-3-nitrobenzoic acid (0.600 g), 5% palladium on carbon (0.600 g), tetrahydrofuran (30 ml) and ethyl acetate (30 ml) was stirred under a hydrogen atmosphere at room temperature and normal pressure for 30 min. Palladium on carbon was filtered off, and the filtrate was concentrated. The residue was purified by silica gel column chromatography (hexane:ethyl acetate=4:1, volume ratio) to give 3-amino-4-[3-(4-chlorophenyl)-1,2,4-oxadiazol-5-yl]benzoic acid (0.15 g, yield 28%). Recrystallization from hexane-tetrahydrofuran gave yellow prism crystals. melting point: 294–296° C. (decomposition).

Example 65

A mixture of methyl 4-[[amino[4-(trifluoromethylphenyl)]methylidene]aminooxycarbonyl]-3-trifluoroacetylaminobenzoate (1.20 g) and xylene (100 ml) was heated under reflux for 3 hrs., while removing the generated water with a Dean-Stark trap. After cooling, the reaction mixture was concentrated, and the residue was purified by silica gel column chromatography (hexane:ethyl acetate=2:1, volume ratio) to give methyl 3-trifluoroacetylamino-4-[3-(4-trifluoromethylphenyl)-1,2,4-oxadiazol-5-yl]benzoate (1.00 g, yield 87%). Recrystallization from hexane-ethyl acetate gave colorless prism crystals. melting point: 188–189° C.

Example 66

A mixture of methyl 3-trifluoroacetylamino-4-[3-(4-trifluoromethylphenyl)-1,2,4-oxadiazol-5-yl]benzoate (0.800 g), 1 M aqueous sodium hydroxide solution (5.1 ml) and tetrahydrofuran (10 ml) was stirred at room temperature for 1 hr. After cooling, 1 M hydrochloric acid was added to acidify the reaction mixture. The crystals were collected by filtration to give 3-amino-4-[3-(4-trifluoromethylphenyl)-1,2,4-oxadiazol-5-yl]benzoic acid (0.570 g, yield 97%). Recrystallization from hexane-tetrahydrofuran gave colorless prism crystals. melting point: >300° C.

Example 67

To a solution (150 ml) of 2-nitro-4-methoxycarbonylbenzoic acid (7.36 g) and N,N-dimethylformamide (0.05 ml) in tetrahydrofuran was added oxalyl chloride (3.14 ml) at 0° C. This mixture was stirred at room temperature for 1 hr., and concentrated. A mixture of the residue, 5-(4-trifluoromethylphenyl)-1H-tetrazole (7.00 g) and pyridine (100 ml) was heated under reflux for 1 hr. After cooling, water was added to the reaction mixture, and the crystals were collected by filtration and purified by silica gel column chromatography (hexane:ethyl acetate=3:1, volume ratio) to give methyl 3-nitro-4-[5-(4-trifluoromethylphenyl)-1,3,4-oxadiazol-2-yl]benzoate (8.15 g, yield 63%). Recrystallization from hexane-ethyl acetate gave colorless prism crystals. melting point: 173–174° C.

Example 68

To a solution (50 ml) of 2-nitro-4-methoxycarbonylbenzoic acid (2.50 g) and an N,N-dimethylformamide (0.05 ml) in tetrahydrofuran was added oxalyl chloride (1.16 ml) at 0° C. This mixture was stirred at room temperature for 1.5 hrs., and concentrated. A mixture of the residue, 5-(4-t-butylphenyl)-1H-tetrazole (2.25 g) and pyridine (30 ml) was heated under reflux for 1 hr. After cooling, water was added to the reaction mixture, and the crystals were collected by filtration and dissolved in ethyl acetate. The organic layer was washed with 1 M hydrochloric acid, water and saturated brine, dried over anhydrous magnesium sulfate and concentrated. The residue was purified by silica gel column chromatography (hexane:ethyl acetate=4:1, volume ratio) to give methyl 4-[5-(4-t-butylphenyl)-1,3,4-oxadiazol-2-yl]-3-nitrobenzoate (3.01 g, yield 71%). Recrystallization from hexane-ethyl acetate gave colorless prism crystals. melting point: 142–143° C.

Example 69

A mixture of methyl 3-nitro-4-[5-(4-trifluoromethylphenyl)-1,3,4-oxadiazol-2-yl]benzoate (2.00 g), 1 M aqueous sodium hydroxide solution (10 ml) and tetrahydrofuran (10 ml) was heated under reflux for 1 hr. After cooling, 1 M hydrochloric acid was added to acidify the reaction mixture. The crystals were collected by filtration and dissolved in ethyl acetate-tetrahydrofuran. This solution was washed with saturated aqueous sodium hydrogen carbonate solution and saturated brine, dried over anhydrous magnesium sulfate, and concentrated to give 3-nitro-4-[5-(4-trifluoromethylphenyl)-1,3,4-oxadiazol-2-yl]benzoic acid (1.20 g, yield 62%). Recrystallization from hexane-tetrahydrofuran gave pale-yellow prism crystals. melting point: 254–255° C.

Example 70

A mixture of methyl 4-[5-(4-t-butylphenyl)-1,3,4-oxadiazol-2-yl]-3-nitrobenzoate (1.50 g), 1 M aqueous sodium hydroxide solution (7.8 ml) and tetrahydrofuran (10 ml) was heated under reflux for 30 min. After cooling, 1 M hydrochloric acid was added to acidify the reaction mixture. The mixture was extracted with ethyl acetate. The organic layer was washed with water and saturated brine, dried over anhydrous magnesium sulfate and concentrated. The residue was purified by silica gel column chromatography (ethyl acetate:methanol=20:1-10:1, volume ratio) to give 4-[5-(4-t-butylphenyl)-1,3,4-oxadiazol-2-yl]-3-nitrobenzoic acid (0.600 g, yield 42%). Recrystallization from hexane-ethyl acetate gave colorless prism crystals. melting point: 233–235° C.

Example 71

A mixture of 3-nitro-4-[5-(4-trifluoromethylphenyl)-1,3,4-oxadiazol-2-yl]benzoic acid (0.600 g), 5% palladium on carbon (0.600 g) and tetrahydrofuran (15 ml) was stirred under a hydrogen atmosphere at room temperature and normal pressure for 30 min. Palladium on carbon was filtered off, and the filtrate was concentrated. The residue was purified by silica gel column chromatography (ethyl acetate:methanol=20:1, volume ratio) to give 3-amino-4-[5-(4-trifluoromethylphenyl)-1,3,4-oxadiazol-2-yl]benzoic acid (0.33 g, yield 59%). Recrystallization from hexane-tetrahydrofuran gave yellow prism crystals. melting point: >300° C.

Example 72

A mixture of 4-[5-(4-t-butylphenyl)-1,3,4-oxadiazol-2-yl]-3-nitrobenzoic acid (0.200 g), 5% palladium on carbon (0.200 g) and tetrahydrofuran (20 ml) was stirred under a hydrogen atmosphere at room temperature and normal pressure for 30 min. Palladium on carbon was filtered off, and the filtrate was concentrated. The residue was purified by silica gel column chromatography (ethyl acetate:methanol=20:1, volume ratio) to give 3-amino-4-[5-(4-t-butylphenyl)-1,3,4-oxadiazol-2-yl]benzoic acid (0.120 g, yield 67%). Recrystallization from hexane-ethyl acetate gave yellow prism crystals. melting point: 266–268° C.

Example 73

To a solution (20 ml) of 4-[5-(4-trifluoromethylphenyl)-2-furyl]benzoic acid -(0.665 g) and N,N-dimethylformamide (0.1 ml) in tetrahydrofuran was added oxalyl chloride (0.209 ml) at 0° C. This mixture was stirred for 10 min., and concentrated. The residue was dissolved in acetonitrile (30 ml), and this solution was added dropwise to 25% aqueous ammonia (50 ml) at 0° C. The mixture was stirred for 10 min. and poured into water. The crystals were collected by filtration and recrystallized from ethanol to give 4-[5-(4-trifluoromethylphenyl)-2-furyl]benzamide (0.506 g, yield 76%) as a colorless crystalline powder. melting point: 263–264° C.

Example 74

A mixture of methyl 4-[5-(4-t-butylphenyl)-1,3,4-oxadiazol-2-yl]-3-nitrobenzoate (0.500 g), 5% palladium on carbon (0.500 g) and tetrahydrofuran (20 ml) was stirred under a hydrogen atmosphere at room temperature and normal pressure for 30 min. Palladium on carbon was filtered off, and the filtrate was concentrated. The residue was purified by silica gel column chromatography (hexane:ethyl acetate=3:1, volume ratio) to give methyl 3-amino-4-[3-(4-t-butylphenyl)-1,2,4-oxadiazol-5-yl]benzoate (0.340 g, yield 74%). Recrystallization from hexane-ethyl acetate gave yellow prism crystals. melting point: 195–196° C.

Example 75

A mixture of methyl 4-[3-(4-chlorophenyl)-1,2,4-oxadiazol-5-yl]-3-nitrobenzoate (0.700 g), 5% palladium on carbon (0.700 g), tetrahydrofuran (15 ml) and ethyl acetate (30 ml) was stirred under a hydrogen atmosphere at room temperature and normal pressure for 30 min. Palladium on carbon was filtered off, and the filtrate was concentrated. The residue was purified by silica gel column chromatography (hexane:ethyl acetate=3:1, volume ratio) to give methyl 3-amino-4-[3-(4-chlorophenyl)-1,2,4-oxadiazol-5-yl]benzoate (0.50 g, yield 79%). Recrystallization from hexane-ethyl acetate gave colorless prism crystals. melting point: 227–228° C.

Example 76

A mixture of methyl 4-[5-(4-trifluoromethylphenyl)-1,3,4-oxadiazol-2-yl]-3-nitrobenzoate (0.500 g), 5% palladium on carbon (0.500 g) and tetrahydrofuran (10 ml) was stirred under a hydrogen atmosphere at room temperature and normal pressure for 30 min. Palladium on carbon was filtered off, and the filtrate was concentrated. The residue was purified by silica gel column chromatography (hexane:ethyl acetate=3:1, volume ratio) to give methyl 3-amino-4-[5-(4-trifluoromethylphenyl)-1,3,4-oxadiazol-2-yl]benzoate (0.36 g, yield 77%). Recrystallization from hexane-ethyl acetate gave yellow prism crystals. melting point: 237–238° C.

Example 77

A mixture of 4-trifluoromethylbenzoyl chloride (2.2 ml), 4-(1,3-dioxolan-2-yl)phenylamidoxime (2.70 g) and pyridine (30 ml) was heated under reflux for 1 hr. After cooling, water was added to the mixture. The obtained crystals were dissolved in tetrahydrofuran (20 ml), and 6 M hydrochloric acid (10 ml) was added. The mixture was stirred overnight at room temperature. The reaction solvent was removed under reduced pressure, and the obtained crystals were collected by filtration and recrystallized from acetone-hexane to give 4-[5-(4-trifluoromethylphenyl)-1,2,4-oxadiazol-3-yl]benzaldehyde (2.64 g, yield 64%) as colorless crystals. melting point: 145–146° C.

Example 78

A mixture of methyl 4-chloroformylbenzoate (2.65 g), 4-phenoxyphenylamidoxime (3.00 g) and pyridine (30 ml) was heated under reflux for 1 hr. After cooling, water was added to the mixture. The crystals were collected by filtration and purified by silica gel column chromatography (hexane:tetrahydrofuran=1:9, volume ratio) to give methyl 4-[3-(3-phenoxyphenyl)-1,2,4-oxadiazol-5-yl]benzoate (4.19 g, yield 86%). Recrystallization from hexane-ethyl acetate gave colorless crystals. melting point:. 132–133° C.

Example 79

A mixture of methyl 4-[3-(3-phenoxyphenyl)-1,2,4-oxadiazol-5-yl]benzoate (1.69 g), 1 M aqueous sodium hydroxide solution (10 ml), methanol (15 ml) and tetrahydrofuran (15 ml) was stirred at 60° C. for 1 hr. After cooling, 1 M hydrochloric acid was added to acidify the reaction mixture. The crystals were collected by filtration and recrystallized from hexane-tetrahydrofuran to give 4-[3-(3-phenoxyphenyl)-1,2,4-oxadiazol-5-yl]benzoic acid (1.35 g, yield 83%) as colorless crystals. melting point: 292–293° C.

Example 80

A mixture of 2-[3-(1,3-dioxolan-2-yl)phenyl]-5-(4-trifluoromethylphenyl)-1,3,4-oxadiazole (4.10 g), 0.5 M sulfuric acid (30 ml) and acetone (100 ml) was heated under reflux for 1 hr. After cooling, the reaction mixture was concentrated, and the residue was diluted with ethyl acetate. This solution was washed with water and saturated brine, dried over anhydrous magnesium sulfate and concentrated to give 3-[5-(4-trifluoromethylphenyl)-1,3,4-oxadiazol-2-yl]benzaldehyde (3.58 g, yield 99%). Recrystallization from hexane-ethyl acetate gave colorless-prism crystals. melting point: 129–130° C.

Example 81

A mixture of 2-[4-(1,3-dioxolan-2-yl)phenyl]-5-(2-nitrophenyl)-1,3,4-oxadiazole (1.75 g), 0.5 M sulfuric acid (15 ml) and acetone (50 ml) was heated under reflux for 1 hr. After cooling, the reaction mixture was concentrated, and the residue was diluted with ethyl acetate. This solution was washed with water and saturated brine, dried over anhydrous magnesium sulfate and concentrated. The residue was purified by silica gel column chromatography (hexane:ethyl acetate=1:1, volume ratio) to give 4-[5-(2-nitrophenyl)-1,3,4-oxadiazol-2-yl]benzaldehyde (1.37 g, yield 89%). Recrystallization from hexane-ethyl acetate gave pale-yellow prism crystals. melting point: 189–190° C.

Example 82

To a solution (20 ml) of 1-[chloro(hydroxyimino)methyl]-4-trifluoromethylbenzene (0.849 g) and 3-ethynylbenzaldehyde (0.521 g) in tetrahydrofuran was added dropwise a solution (10 ml) of triethylamine (1.12 ml) in tetrahydrofuran at 0° C. This mixture was stirred overnight at room temperature and poured into water. The mixture was extracted with ethyl acetate. The organic layer was washed with water and saturated brine, dried over anhydrous magnesium sulfate and concentrated. The residue was purified by silica gel column chromatography (hexane:ethyl acetate=4:1, volume ratio) and recrystallized from hexane-ethyl acetate to give 3-[3-(4-trifluoromethylphenyl)-5-isoxazolyl]benzaldehyde (0.660 g, yield 52%) as colorless needle crystals. melting point: 151–152° C.

Formulation Example 1

(Production of Capsules)

| | | |
|---|---|---|
| (1) Compound of Example 1 | | 30 mg |
| (2) Microcrystalline cellulose | | 10 mg |

|   |   |   |
|---|---|---|
| (3) Lactose | | 19 mg |
| (4) Magnesium stearate | | 1 mg |
| total | | 60 mg |

(1), (2), (3) and (4) are admixed and filled in a gelatin capsule.

Formulation Example 2

(Production of Tablets)

|   |   |   |
|---|---|---|
| (1) Compound of Example 1 | | 30 g |
| (2) Lactose | | 50 g |
| (3) Corn starch | | 15 g |
| (4) Carboxymethylcellulose calcium | | 44 g |
| (5) Magnesium stearate | | 1 g |
| 1000 tablets | total | 140 g |

The entire amount of 1), 2) and 3) and 30 g of 4) are admixed with water. After drying in vacuo, the mixture is granulated. Thereto are added 14 g of (4) and 1 g of (5), and the mixture is tableted with a tableting machine. In this way, 1,000 tablets containing 30 mg of the compound of Example 1 per tablet are obtained.

INDUSTRIAL APPLICABILITY

The compound of the present invention has glucose-lowering action, lipid-lowering action, blood insulin lowering action, insulin resistance improving action, insulin sensitizing action and retinoid-related receptor (except retinoic acid receptors) function regulating activity.

Therefore, the compound of the present invention can be used as an agent for the prophylaxis or treatment of, for example, diabetes mellitus (e.g., type I diabetes mellitus, type II diabetes mellitus, gestational diabetes mellitus etc.); an agent for the prophylaxis or treatment of hyperlipidemia (e.g., hypertriglyceridemia, hypercholesterolemia, hypo-high-density-lipoproteinemia, postprandial hyperlipidemia etc.); an agent for improving insulin resistance; an insulin sensitizer; an agent for the prophylaxis or treatment of impaired glucose tolerance [IGT]; and an agent for preventing progress from impaired glucose tolerance to diabetes mellitus.

The invention claimed is:

1. A method for the treatment of obesity in a mammal, which comprises administering, to the mammal, a peroxisome proliferator-activated receptor transcriptional activity promoter which is non-binding to peroxisome proliferator-activated receptors, wherein the peroxisome proliferator-activated receptor transcriptional activity promoter is a compound represented by the formula:

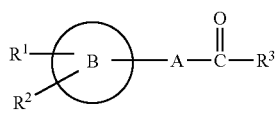

(I)

wherein
one of $R^1$ and $R^2$
is an optionally substituted monocyclic aromatic hydrocarbon group or an optionally substituted monocyclic aromatic heterocyclic group containing one heteroatom, and the other is a hydrogen atom, a halogen atom or an optionally substituted hydrocarbon group;

B is a furan;

A is an optionally substituted phenyl group; and $R^3$ is —$OR^4$ ($R^4$ is a hydrogen atom or an optionally substituted hydrocarbon group), or a salt thereof.

* * * * *

```
                               SEQUENCE LISTING

<160> NUMBER OF SEQ ID NOS: 8

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1
gtgggtaccg aaatgaccat ggttgacaca gag                                     33

<210> SEQ ID NO 2
<211> LENGTH: 33
<212> TYPE: DNA
<213> ORGANISM: Artificial
<220> FEATURE:
<223> OTHER INFORMATION: primer

<400> SEQUENCE: 2
ggggtcgacc aggactctct gctagtacaa gtc                                     33

<210> SEQ ID NO 3
<211> LENGTH: 33
<212> TYPE: DNA
<213> ORGANISM: Artificial
<220> FEATURE:
<223> OTHER INFORMATION: primer

<400> SEQUENCE: 3
ttagaattcg acatggacac caaacatttc ctg                                     33

<210> SEQ ID NO 4
<211> LENGTH: 33
<212> TYPE: DNA
```

```
<213> ORGANISM: Artificial
<220> FEATURE:
<223> OTHER INFORMATION: primer

<400> SEQUENCE: 4
cccctcgagc taagtcattt ggtgcggcgc ctc                    33

<210> SEQ ID NO 5
<211> LENGTH: 36
<212> TYPE: DNA
<213> ORGANISM: Artificial
<220> FEATURE:
<223> OTHER INFORMATION: primer

<400> SEQUENCE: 5
tcgacagggg accaggacaa aggtcacgtt cgggag                 36

<210> SEQ ID NO 6
<211> LENGTH: 36
<212> TYPE: DNA
<213> ORGANISM: Artificial
<220> FEATURE:
<223> OTHER INFORMATION: primer

<400> SEQUENCE: 6
tcgactcccg aacgtgacct ttgtcctggt ccctg                  36

<210> SEQ ID NO 7
<211> LENGTH: 28
<212> TYPE: DNA
<213> ORGANISM: Artificial
<220> FEATURE:
<223> OTHER INFORMATION: primer

<400> SEQUENCE: 7
cccagatctc cccagcgtct tgtcattg                          28

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
tcaccatggt caagcttta agcgggtc                           28
```